(12) United States Patent
Postma

(10) Patent No.: US 12,085,558 B2
(45) Date of Patent: Sep. 10, 2024

(54) DEVICES FOR SINGLE-MOLECULE SEQUENCING, INCLUDING RELATED METHODS AND PROCESSES

(71) Applicant: The California State University—Northridge, Northridge, CA (US)

(72) Inventor: Hendrik Postma, Northridge, CA (US)

(73) Assignee: The Trustees of the California State University, Long Beach, CA (US)

( * ) Notice: Subject to any disclaimer, the term of this patent is extended or adjusted under 35 U.S.C. 154(b) by 171 days.

(21) Appl. No.: 17/176,371

(22) Filed: Feb. 16, 2021

(65) Prior Publication Data

US 2022/0326214 A1    Oct. 13, 2022

Related U.S. Application Data

(60) Provisional application No. 62/976,948, filed on Feb. 14, 2020.

(51) Int. Cl.
| | |
|---|---|
| *G01N 33/487* | (2006.01) |
| *B82Y 15/00* | (2011.01) |
| *C12Q 1/6869* | (2018.01) |
| *G01N 27/327* | (2006.01) |

(52) U.S. Cl.
CPC ..... *G01N 33/48721* (2013.01); *C12Q 1/6869* (2013.01); *G01N 27/3278* (2013.01); *B82Y 15/00* (2013.01)

(58) Field of Classification Search
None
See application file for complete search history.

(56) References Cited

PUBLICATIONS

P. Puczkarski, et al., "Low-Frequency Noise in Graphene Tunnel Junctions", ACS Nano, 12(9): p. 9451-9460, August (Year: 2018).*
Postma, H. W. C. (2008). Rapid Sequencing of Individual DNA Molecules in Graphene Nanogaps. arxiv.org/abs/0810.3035.

(Continued)

*Primary Examiner* — J. Christopher Ball
(74) *Attorney, Agent, or Firm* — Sandra Poteat Thompson; Finlayson Toffer Roosevelt & Lilly LLP

(57) ABSTRACT

Processes for conductive material nanogap formation have been developed that include: providing a base material, wherein the base material is either solid or comprises a micropore that extends through the first layered material, and wherein the micropore comprises a top opening, a bottom opening, and a volume boundary, applying a conductive material sheet to the first layered material, wherein the conductive material sheet covers the top opening of the micropore, applying two conducting electrodes to the conductive material sheet, so that each one of the conducting electrodes is positioned on either side of the micropore, applying an etch mask that covers at least a part of the conductive material sheet, the top opening of the micropore (if present), or a combination thereof, applying a passivation layer over at least the etch mask, fabricating a hole in the passivation layer directly above the top opening of the micropore, and applying at least one voltage pulse through the at least one conducting electrode to create a nanogap in the conductive material sheet, wherein the nanogap is over and open to the top opening of the micropore. In some embodiments, the micropore and the nanogap are fabricated simultaneously.

23 Claims, 11 Drawing Sheets

Specification includes a Sequence Listing.

A: graphene on insulator

B: electrodes

C: etch mask

D: top insulator

E: self aligned micropore

(56) References Cited

PUBLICATIONS

Postma, H. W. C. (2010). Rapid Sequencing of Individual DNA Molecules in Graphene Nanogaps. Nano Letters, 10(2):420-425.

Prasongkit, J., et al. (2015). Theoretical assessment of feasibility to sequence DNA . . . Scientific Reports, 5.

Prasongkit, J., et al. (2011). Transverse Conductance of DNA Nucleotides in a Graphene Nanogap from First Principles. Nano Letters, 11(5):1941-1945.

Scarpa, F., Adhikari, S., and Phani, A. S. (2009). Effective elastic mechanical properties of single layer graphene sheets. Nanotechnology, 20(6):065709.

Smeets, R. M. M., et al. (2006). Salt Dependence of Ion Transport and DNA Translocation through Solid-State Nanopores. Nano Letters, 6(1):89-95.

Storm, A. J., et al. (2005). Translocation of doublestrand DNA through a silicon oxide nanopore. Physical Review E, 71(5):051903.

Tsutsui, M., Taniguchi, M., Yokota, K., and Kawai, T. (2010). Identifying single nucleotides by tunnelling current. Nat Nano, 5(4):286-290.

Kowalczyk, S. W., Tuijtel, M. W., Donkers, S. P., and Dekker, C. (2010). Unraveling Single-Stranded DNA in a Solid-State Nanopore. Nano Letters, 10(4):1414-1420.

Lee, C., Wei, X., Kysar, J. W., and Hone, J. (2008). Measurement of the Elastic Properties and Intrinsic Strength of Monolayer Graphene. Science, 321(5887):385-388.

Li, J., Stein, D., McMullan, C., Branton, D., Aziz, M. J., and Golovchenko, J. A. (2001). Ion-beam sculpting at nanometre length scales. Nature, 412(6843):166-169.

Meller, A., et al. (2000). Rapid nanopore discrimination between single polynucleotide molecules. Proceedings of the National Academy of Sciences, 97(3):1079-1084.

Meller, A., Nivon, L., and Branton, D. (2001). Voltage-Driven DNA Translocations through a Nanopore. Physical Review Letters, 86(15):3435.

Ohshiro, T., et al (2012); Single-molecule electrical random resequencing of DNA and RNA. Scientific reports, 2:501.

Poot, M. and van der Zant, H. S. J. (2008). Nanomechanical properties of few-layer graphene membranes. Applied Physics Letters, 92(6):063111-3.

Ohshiro, T., et al. (2014). Detection of post-translational modifications in single peptides using electron tunnelling currents. Nature Nanotechnology, 9(10):835-840.

Patel, H. N., et al. (2017). DNA-graphene interactions during translocation through nanogaps. Plos One, 12(2):e0171505.

Akeson, M., et al. (1999). Microsecond time-scale discrimination . . . Biophysical journal, 77(6):3227-33.

Amorim, R. G., et al. (2016). Boosting DNA Recognition Sensitivity of Graphene Nanogaps through Nitrogen Edge Functionalization. The Journal of Physical Chemistry C.

Bunch, J. S., et al. (2008). Impermeable Atomic Membranes from Graphene Sheets. Nano Letters, 8(8):2458-2462.

Butler, T. Z., et al. (2006). Determination of RNA Orientation during Translocation through a Biological Nanopore. Biophysical Journal, 90(1):190-199.

Chang, S., He, J., Kibel, A., Lee, M., Sankey, O., Zhang, P., and Lindsay, S. (2009). Tunnelling readout of hydrogen-bonding-based recognition. Nature Nanotechnology, 4:297.

Deamer, D. W. and Branton, D. (2002). Characterization of nucleic acids by nanopore analysis. Acc. Chem. Res, 35(10):817-825.

Dekker, C. (2007). Solid-state nanopores. Nat. Nanotechnol, 2:209-215.

Hall, J. E. (1975). Access resistance of a small circular pore. Journal of General Physiology, 66(4):531.

Kasianowicz, J., et al. (1996). Characterization of individual polynucleotide molecules using a membrane channel. Proc. Nati. Acad. Sci., 93(24):13770-13773.

Koenig, S. P., Boddeti, N. G., Dunn, M. L., and Bunch, J. S. (2011). Ultrastrong adhesion of graphene membranes. Nat Nano, 6:543-546.

* cited by examiner

DEVICES FOR SINGLE-MOLECULE SEQUENCING, INCLUDING RELATED METHODS AND PROCESSES

This application is a United States Utility Patent Application that claims priority to U.S. Provisional Patent Application Ser. No. 62/976,948 filed on Feb. 14, 2020 and entitled "Device for Single-Molecule Sequencing", which is commonly owned and incorporated here in its entirety by reference.

FIELD OF THE SUBJECT MATTER

The field of the subject matter is devices, processes, and methods for single-molecule sequencing, which includes, but is not limited to, macromolecules.

BACKGROUND

One of the greatest challenges of biotechnology is establishing the base sequence of individual molecules of DNA without the need for PCR amplification or other modification of the molecule. The Sanger method has proven extremely powerful and has resulted in the recent sequencing of the human genome in a monumental collaborative effort.

Sequencing human DNA occurs through shotgun sequencing which is a strategy around the technique introduced more than 30 years ago by Sanger et al. It consists of breaking the sample into small random fragments and amplifying them, sequencing these fragments using the Sanger method, and merging these sequences by determining overlapping areas by their base sequence. There are many challenges to making current sequencing technology more cost effective and comprehensive. 1) The total process is time and resource intensive because the Sanger read length is short, requiring many small sequencing steps, many overlapping reads, and a lot of computational power to merge the sequences. 2) DNA amplification is required. Bacterial cloning with *E. coli* sometimes contaminates read sequences with bacterial material. PCR sometimes creates artificially long repetitive segments due to polymerase stuttering, or merges two unrelated sequences thereby creating a DNA segment that does not occur in the original sequence. In addition, it is a time and cost-intensive process and since it is at the heart of the sequencing process, it quickly increases the overall cost and time required for whole-genome sequencing. 3) The samples need to be tagged with fluorescent or radioactive labels to image the DNA fragments after gel electrophoresis. 4) It is not possible to sequence large homopolymeric segments, e.g. telomeres, of the genome due to the finite Sanger read length.

Using the requirement of the X-prize, to sequence 100 genomes in 10 days, as a benchmark for future sequencing technology with a single device that will sequence all of these genomes sequentially, without any pre- or post-processing, an approximately 3 µs read time per base is required.

Numerous improvements are being developed, optimizing various aspects of the sequencing process. Miniaturization with microfluidics is being developed to improve the readout speed, reduce the volume of material needed, and reduce the cost per base sequenced, while still relying on the proven Sanger method. Also, reversible terminators are being developed which will allow for sequencing of homopolymeric sequences. Finally, several single-molecule sequencing techniques are being developed. These represent a different strategy that deviate from the Sanger method. They require very little genome material and therefore no amplification. One such method demonstrated single-nucleotide microscopy of fluorescently labeled nucleotides that were inserted into individual DNA molecules.

Nanopore-based sequencing is a single-molecule sequencing technique that is especially promising. It is believed that a large read length and high throughput can be achieved simultaneously. The first translocation studies of individual DNA molecules were conducted with naturally occurring alpha-hemolysin (αHL) proteins that spontaneously embed themselves in a lipid bilayer and form a nanopore. This αHL pore is studied using electrophysiology, in which a patch-clamp amplifier records the current through the protein pore while a DNA molecule translocates through it under the influence of an applied transmembrane electric field acting on the negatively charged backbone. Both single-stranded DNA (ssDNA) and double-stranded DNA (dsDNA) have been studied. The minimum pore size that ssDNA can translocate through is 1.5 nm while it is 3 nm for dsDNA.

Biological nanopores and the lipid bilayer membrane they are embedded in are only stable within a small range of temperature, pH, chemical environments, and applied electric fields, limiting practical applications. Solid-state nanopores do not suffer from this. Solid-state nanopores have been fabricated in Si3N4 membranes, SiO2 membranes, and polymer films. Translocation studies of dsDNA showed very high velocities, owing to the much-reduced interaction of DNA with solid-state nanopores as compared to αHL pores.

Nanopore-based sequencing using a transverse conductance measurement of a DNA molecule while it translocates through the nanopore has been suggested as an alternative to the Sanger method. The idea is that different bases have different local electronic densities of states with different spatial extent owing to their different chemical composition. If the bases are passing through a voltage-biased tunnel gap one by one, they will periodically alter the current based on whether the localized states in the bases are contributing to the tunnel current. Analyzing the current as a function of base is then expected to reveal the base sequence. However, making nano-electrodes that are aligned with the nanopore is very challenging.

One design that can be utilized is one that incorporates graphene nanogaps for DNA sequencing, utilizing the graphene as a conductor/electrode, as well as the membrane material. Graphene, a single-atom thick hexagonal carbon lattice that has recently been discovered, can be synthesized in a variety of manners. It is an ideal material for making nanogaps for sequencing due to its single-atom thickness d, its ability to survive large transmembrane pressures, and its intrinsic conducting properties. The last property is especially advantageous because the membrane is the electrode, automatically solving the problem of having to fabricate nanoelectrodes that are carefully aligned with a nanogap. Contacts to the graphene sheet can be fabricated using standard electron-beam lithography, metal evaporation and lift off.

Conventional methods that have been used to obtain graphene nanogaps include nanolithography with a scanning tunneling microscope (STM), in a method similar to that used for cutting carbon nanotubes. STM nanolithography on the top graphene layer of graphite was demonstrated. The ideal nanogap width is 1.5-2.0 nm, allowing for ss-DNA to pass through it in an unfolded state as well as assuring the largest transverse current. The transverse conductance of DNA molecules can then be measured while they translocate through a nanogap in the graphene membrane, revealing the base sequence of the molecule.

The DNA translocation speed is typically much larger in solid-state nanopores than in biological nanopores, owing to their large difference in size and aspect ratio. For pore sizes that are small compared to the ssDNA width, the bases stick to the side of the nanogap, lagging behind the backbone, while the molecule moves through the gap. For large gap sizes, the bases' orientation can vary significantly, but they can be aligned by the electric field due to the applied bias voltage $V_{bias}$ across the gap.

When large (~10-100 kbp) dsDNA translocates through solid-state nanopores with a diameter much wider than the molecule, the velocity depends as a power-law on the length:

$$v \propto L^{2v-1} = L^{-0.27}$$

where v=0.611 is the Flory exponent and the required applied electric field strength is relatively low, E=6.0×10⁶ V/m. In contrast, 'long' (>>12 nt) ss-DNA translocates through a much more narrow (1.8 nm) and d=5.2 nm deep αHL nanopore with length-independent velocity. The velocity depends quadratically on a much larger required driving voltage V as:

$$v = k_1(V-E_0/d)^2 + k_2$$

where $E_0/d$=47 mV, $k_2$=0.006 nm/μs, and $k_1$=2.0 nm/usV². The electric field threshold for DNA translocation $E_0$, depends on the pH and pore geometry and is due to a stretching transition of the molecule into the pore.

The αHL pore geometry is very close to that proposed here, since 1) the ideal graphene nanogap width of 1.5 nm is similar and 2) the narrowest region of the αHL pore and the graphene nanogap are similar in thickness. This may result in similar DNA-graphene nanogap interaction strengths although a full model is required. An advantage of graphene nanogaps is then that their local atomic configuration can be imaged directly with the STM after the gap has been fabricated allowing for a comprehensive comparison of measurements with theoretical calculations. Assuming an average field strength in the αHL pore of 250 mV/5.2 nm=48MV/m, we can extrapolate that an applied voltage of 30 mV across the graphene membrane with effective thickness of 0.6 nm will yield an average translocation time of 3.6 μs/nt. The voltage that is applied across the nanogap to read the DNA's transverse conductance is expected to slightly alter the translocation velocity.

It has been suggested that the conduction mechanism that allows one to distinguish between the different bases depends on the spatial extend of the HOMO and LUMO levels (which are typically far away from the fermi level of the leads) and their overlap with the electrode wavefunction. More recently, it was found that poly(GC) and poly(AT) can be distinguished electronically through measurement of localized states around around $V_{bias}$=0. One can then estimate the current due to the bases by evaluating:

$$I = A \int D_L(E) D_R(E-eV_{bias}) |T(E)|^2 dE$$

where T(E) is the effective transmission of the electronic base states, and $D_{L,R}$ are the densities of states of the left and right electrodes, respectively. For a realistic description of the tunnel current in the proposed experiment, both the distance dependence for this resonant-tunneling regime, counter ions, and the unique density of states of graphene to be taken into account.

To this end, it would be desirable to a) develop a process for making the graphene nanogaps with the required geometry and critical dimensions using an electrical breaking protocol; b) develop a process for making the devices accessible to liquids, while insulating the electronics, by geometrically biasing the nanogap formation over liquid accessible parts of the device; c) develop a process for layering the functional components that enables the reliable assembly of the device; d) develop a process for inhibition of mechanical fluctuations of the device by controlling the size of the thinnest mechanically cantilevered components; e) develop a process for querying the high impedance high frequency properties of a molecule using the nonlinear characteristics of the device as a mixer; f) develop and design an instrument for the required low noise measurement using a high speed amplifier; g) develop a process for controlling the molecules and querying them in a linear fashion by chemically, thermally, and electrostatically keeping them separated and in linear form; h) develop a process for chemically stabilizing the graphene edges by binding groups to the dangling carbon bonds; i) develop a method for extraction of the real time clock of molecules by monitoring the high frequency pulsing behavior of the molecule as it goes through the device; j) develop and design a device that is planar enough for the querying of long molecules without an entropic barrier; and k) develop a method for fast readout that avoids base fluctuations.

SUMMARY OF THE SUBJECT MATTER

Processes for conductive material nanogap formation have been developed that include: providing a base material, wherein the base material comprises a micropore that extends through the first layered material, and wherein the micropore comprises a top opening, a bottom opening, and a volume boundary, applying a conductive material sheet to the first layered material, wherein the conductive material sheet covers the top opening of the micropore, applying two conducting electrodes to the conductive material sheet, so that each one of the conducting electrodes is positioned on either side of the micropore, applying an etch mask that covers at least a part of the conductive material sheet, the top opening of the micropore, or a combination thereof, applying a passivation layer over at least the etch mask, fabricating a hole in the passivation layer directly above the top opening of the micropore, and applying at least one voltage pulse through the at least one conducting electrode to create a nanogap in the conductive material sheet, wherein the nanogap is over and open to the top opening of the micropore.

Additional processes for conductive material nanogap formation have been developed that include: providing a base material, applying a conductive material sheet to the base material, applying two conducting electrodes to the conductive material sheet, applying an etch mask that covers the at least one conducting electrode and at least a part of the conductive material sheet to form a second layered material, applying a second insulating layer to the second layered material to form a third layered material, fabricating a micropore in the third layered material, and simultaneously fabricating a nanogap in the conductive material sheet, wherein the nanogap is smaller in diameter than the micropore.

DETAILED DESCRIPTION

Figure 1:
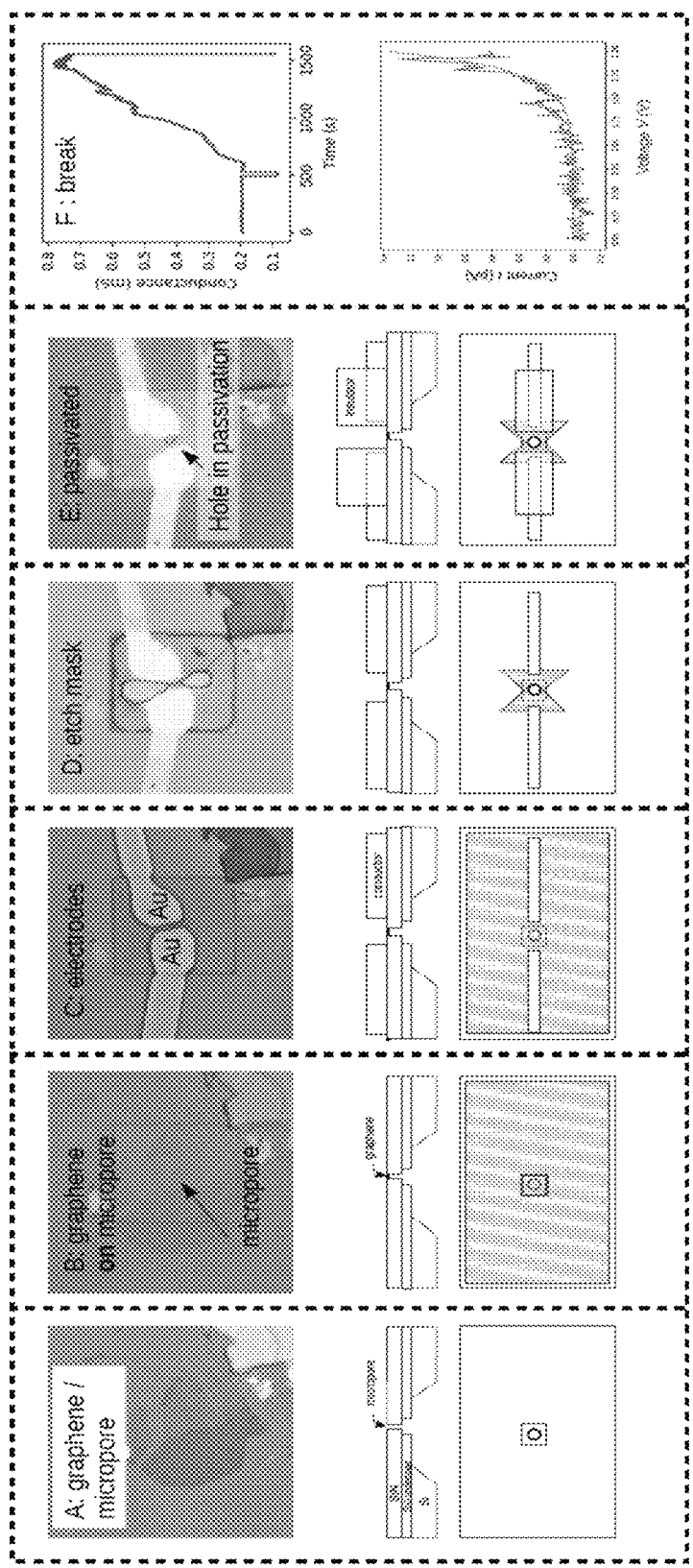
FIG. 1 shows a graphene nanogap fabrication procedure. A) (top) a graphene sheet is identified by its optical image contrast. (bottom) micropore is fabricated in a thin SiN membrane on a supporting substrate. B) The graphene sheet is covering the micropore. C) Conducting electrodes are fabricated on the graphene sheet on either side of the micropore. D) A tapered etch mask is fabricated that has the narrowest taper over the micropore. E) A passivation layer is placed over the entire device and a hole is fabricated over the micropore/graphene hole. F) Voltage pulses are used to create a gap in the graphene that is over the device and the I(V) characteristic measurement is used to determine the nanogap size through a Simmons model fit.

Contemplated devices, processes, and methods build on more than two decades worth of work on DNA translocation through nanopores (Kasianowicz et al., 1996; Akeson et al., 1999; Meller et al., 2000, 2001; Deamer and Branton, 2002; Li et al., 2001; Storm et al., 2005; Butler et al., 2006). The technique described here is based on a tunneling read of the transverse conductance of the individual bases, as opposed to reading the ion current. Tunneling approaches are pursued by various groups and single-nucleotide resolution has been demonstrated on immobilized DNA molecules (Chang et al., 2009; Tsutsui et al., 2010). Graphene is an ideal material for making nanogaps for sequencing due to 1) its single-atom thickness that enables transverse conductance measurements with single-base resolution, in contrast to solid-state nanopores modified for transverse measurements, 2) its ability to survive large transmembrane pressures (Bunch et al., 2008; Poot and van der Zant, 2008; Lee et al., 2008; Scarpa et al., 2009; Koenig et al., 2011), and 3) its intrinsic conducting properties. This last property is especially advantageous because the membrane is the electrode, automatically solving the problem of having to fabricate nanoelectrodes that are exactly aligned with a nanogap. The ideal nanogap size is 1.0-1.6 nm (Postma, 2010). Subsequent theoretical studies support graphene-nanogap's potential for DNA sequencing as well (Prasongkit et al., 2011, 2015; Amorim et al., 2016). Transverse conductance measurements have also been explored by the group of Kawai in a metal break junction and the first results look promising (Ohshiro et al., 2012, 2014), but a deliberate direct read complete sequencing through tunneling has not been achieved yet.

A technique for rapid DNA sequencing with graphene nanogaps (Postma, 2008) was initially generally proposed in 2008. The first parameters were determined in 2010 (Postma, 2010), and subsequent studies of nanogap fabrication and demonstrated DNA translocation (Patel et al., 2017) have led to the specific approach disclosed herein.

In this disclosure, it will be clear that the inventors have: a) developed a process for making the graphene nanogaps with the required geometry and critical dimensions using an electrical breaking protocol; b) developed a process for making the devices accessible to liquids, while insulating the electronics, by geometrically biasing the nanogap formation over liquid accessible parts of the device; c) developed a process for layering the functional components that enables the reliable assembly of the device; d) developed a process for inhibition of mechanical fluctuations of the device by controlling the size of the thinnest mechanically cantilevered components; e) developed a process for querying the high impedance high frequency properties of a molecule using the nonlinear characteristics of the device as a mixer; f) developed and designed an instrument for the required low noise measurement using a high speed amplifier; g) developed a process for controlling the molecules and querying them in a linear fashion by chemically, thermally, and electrostatically keeping them separated and in linear form; h) developed a process for chemically stabilizing the graphene edges by binding groups to the dangling carbon bonds; i) developed a method for extraction of the real time clock of molecules by monitoring the high frequency pulsing behavior of the molecule as it goes through the device; j) developed and designed a device that is planar enough for the querying of long molecules without an entropic barrier; and k) developed a method for fast readout that avoids base fluctuations.

A contemplated conductive material or graphene nanogap fabrication process we have developed relies on the breakdown of narrow graphene ribbons with short high voltage pulses in an inert atmosphere. After breaking, the same electrodes that are used for breaking can be used for extraction of the I(V) characteristic, which is then used for determining the nanogap width. The unique aspect of this approach is 1) that it is a completely hands-off approach that can be performed on a wafer scale in massively parallel fashion, 2) it leads to self-aligned graphene electrodes, and 3) that the nanogap width is determined by the pulse voltage and duration. This procedure also self-cleans the graphene surface from organic residue due to the raised temperature during nanogap formation.

Specifically, FIG. 1 shows a graphene nanogap fabrication procedure. A) (top) a graphene sheet is identified by its optical image contrast. (bottom) micropore is fabricated in a thin SiN membrane on a supporting substrate. B) The graphene sheet is covering the micropore. C) Conducting electrodes are fabricated on the graphene sheet on either side of the micropore. D) A tapered etch mask is fabricated that has the narrowest taper over the micropore. E) A passivation layer is placed over the entire device and a hole is fabricated over the micropore/graphene hole. F) Voltage pulses are used to create a gap in the graphene that is over the device and the I(V) characteristic measurement is used to determine the nanogap size through a Simmons model fit.

Specifically, processes and related methods for conductive material nanogap formation have been developed that include: providing a base material, wherein the base material comprises a micropore that extends through the first layered material, and wherein the micropore comprises a top opening, a bottom opening, and a volume boundary, applying a conductive material sheet to the first layered material, wherein the conductive material sheet covers the top opening of the micropore, applying two conducting electrodes to the conductive material sheet, so that each one of the conducting electrodes is positioned on either side of the micropore, applying an etch mask that covers at least a part of the conductive material sheet, the top opening of the micropore, or a combination thereof, applying a passivation layer over at least the etch mask, fabricating a hole in the passivation layer directly above the top opening of the micropore, and applying at least one voltage pulse through the at least one conducting electrode to create a nanogap in the conductive material sheet, wherein the nanogap is over and open to the top opening of the micropore.

It should be understood that in some contemplated embodiments, the conductive material sheet may be etched, shaped, fabricated first with electrode deposition or application following that etching, shaping, fabricating step.

In contemplated embodiments, nanogaps are created as a part of a conductive material. In some of these contemplated embodiments, the conductive material comprises graphene. It should be understood that any suitable conductive material will be suitable for these applications and devices.

In contemplated embodiments, a base material is included as a starting point in the process or as a base to contemplated devices. The base material may be one material or may be a layered material that comprises at least two different materials, such as a substrate and an insulating layer. In some contemplated embodiments, the base material may comprise at least two layers, wherein the at least two layers may comprise a substrate, a thin membrane that is applied to or coupled with the substrate to form a first layered material, at least one insulating layer, at least one additional layer of material, or a combination thereof. Contemplated base materials may include silicon, carbon, nitrogen, oxygen, or other suitable materials.

In each of the contemplated processes, at least one micropore is present already or fabricated as part of the nanogap formation (simultaneously). Contemplated micropores comprise a top opening, a bottom opening, and a volume boundary. As contemplated, the phrase "volume boundary" means the physical boundary that encloses the space of the micropore between the top opening and the bottom opening.

One contemplated feature of embodiments presented herein is the presence, application, and use of conducting electrodes. In some embodiments, at least two conducting electrodes are applied and positioned on either side of the micropore, if a micropore is present. In other embodiments, they are applied to one of the layers at some point during the layering process. Contemplated conducting electrodes can be used in a number of different ways, including formation of the nanogap, formation of the nanogap and micropore, determining the width of the nanogap in the conductive material sheet, to provide a heat sink to keep the device at an ambient temperature, to provide a voltage source to aid in the molecule and macromolecule translocation and identification process discussed herein. In contemplated embodiments and processes disclosed herein, the at least one conducting electrode is positioned at least a first distance away from the volume boundary of the micropore. It should be understood that if one conducting electrode is utilized, there may be another way to provide a corresponding conducting match, such as a salt bath.

Another contemplated layer or feature of contemplated embodiments is an etch mask that is used in the fabrication stage/stages of the micropore and/or nanogap. Etch masks are utilized to restrict the etching of a substrate or layered materials in or to some areas. There are a number of different steps contemplated herein where the etch mask can be applied in order to arrive at the same micropore and nanogap arrangement. As disclosed herein, the etch mask may be tapered. In some embodiments, a contemplated etch mask may cover at least one of the conducting electrodes.

Contemplated nanogaps in conductive material sheets are formed when the conductive material sheet is heated above an ambient temperature before fabricating a hole in the passivation layer directly above the top opening of the micropore, if a micropore is present. Contemplated nanogaps comprise a top side and a bottom side and comprises a width. Contemplated nanogaps also comprise a first distance on the conductive material or graphene sheet between an edge of the nanogap and an edge of an insulating material. In some contemplated nanogaps, the top side and the bottom side of the nanogap, along with the first distance is accessible and able to interact with a liquid, which is very important when looking at applications of the nanogap structure later described herein.

Contemplated nanogaps are utilized in macromolecule or molecule translocation devices, wherein these devices are nonlinear.

Additional processes and related methods for conductive material nanogap formation have been developed that include: providing a base material, applying a conductive material sheet to the base material, applying two conducting electrodes to the conductive material sheet, applying an etch mask that covers the at least one conducting electrode and at least a part of the conductive material sheet to form a second layered material, applying a second insulating layer to the second layered material to form a third layered material, fabricating a micropore in the third layered material, and simultaneously fabricating a nanogap in the conductive material sheet, wherein the nanogap is smaller in diameter than the micropore. As shown, in this contemplated process, a nanogap is simultaneously fabricated with the micropore.

Graphene typically has wrinkles and fold with typical distance $d_{wrinkle}$. These wrinkles can lead to resistance in the devices, which make them not useful for sequencing devices. Further, the wrinkles represent undesirable slack in the device that could compromise the mechanical stability of the device. The process described here therefore requires electrodes that are close enough together such that the probability of having a wrinkle in between the electrodes is very low. Therefore, the device requires $d_1 < d_{wrinkle}$.

Figure 2:
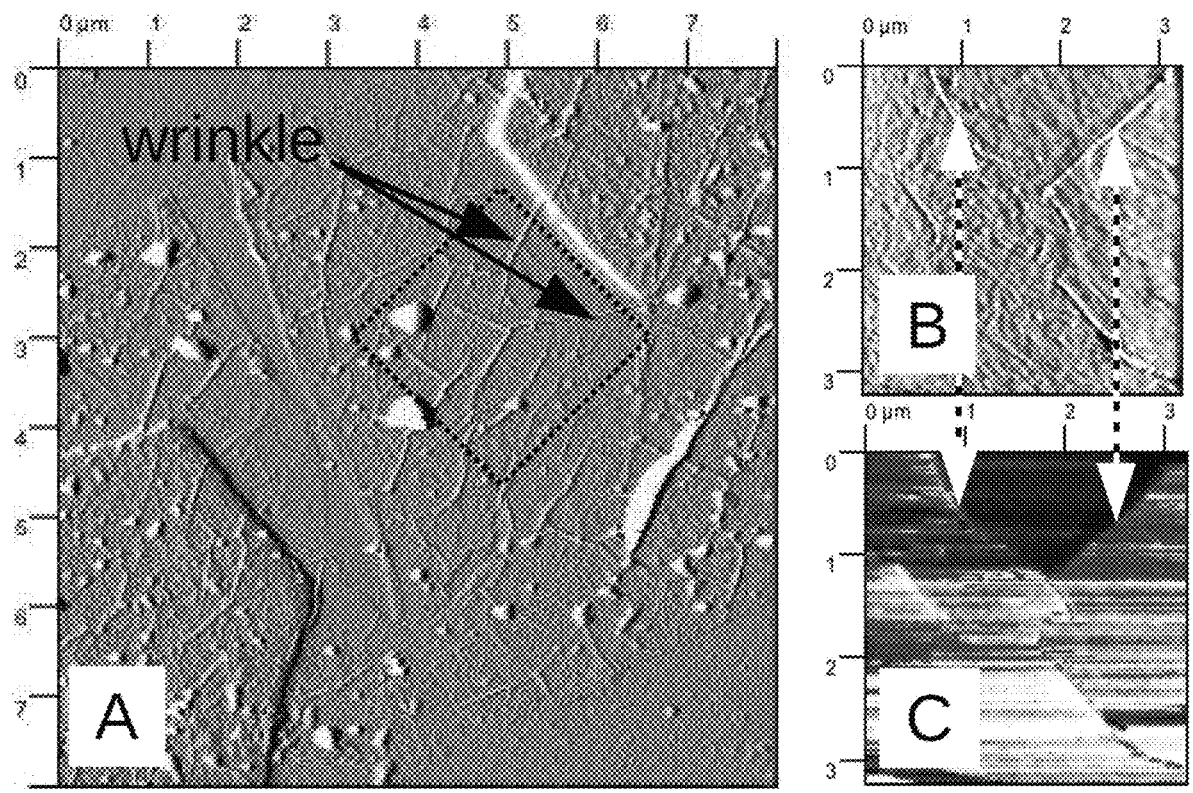
FIG. 2 shows A) Tapping mode atomic force amplitude micrograph of graphene on a solid substrate with wrinkles. The top right electrode is connected to a voltage source. Dashed square shows the area selected for imaging in B and C. B) Contact mode atomic force micrograph of zoomed in selection from A. C) Conducting-mode atomic force micrograph of same area in B. The current is measured with the tip of the microscope. The current is largest closest to the electrode, due to the resistive effect of the indicated wrinkles (dashed arrows).

Specifically, FIG. 2 shows A) Tapping mode atomic force amplitude micrograph of graphene on a solid substrate with wrinkles. The top right electrode is connected to a voltage source. Dashed square shows the area selected for imaging in B and C. B) Contact mode atomic force micrograph of zoomed in selection from A. C) Conducting-mode atomic force micrograph of same area in B. The current is measured with the tip of the microscope. The current is largest closest to the electrode, due to the resistive effect of the indicated wrinkles (gray arrows).

As part of the contemplated embodiments disclosed herein, a technique has been developed for tapering the graphene ribbon to a narrow point that is aligned over a hole in the supporting membrane. In this manner, the nanogap automatically forms over the freely suspended section.

In order to break the graphene by running large currents through it, the center of the graphene sheet over the micropore needs to get hot enough for the device to break in a controlled manner. The metal electrodes provide heat sinks that keep the device at the ambient temperature. The heat is provided by the electron bath so therefore needs to couple of the phonon bath so the device can get hot enough and break. This occurs on a length scale set by the electron-phonon mean free path $l_{e-ph}$. Therefore, the device requires $d1 > l_{e-ph}$.

Figure 3:
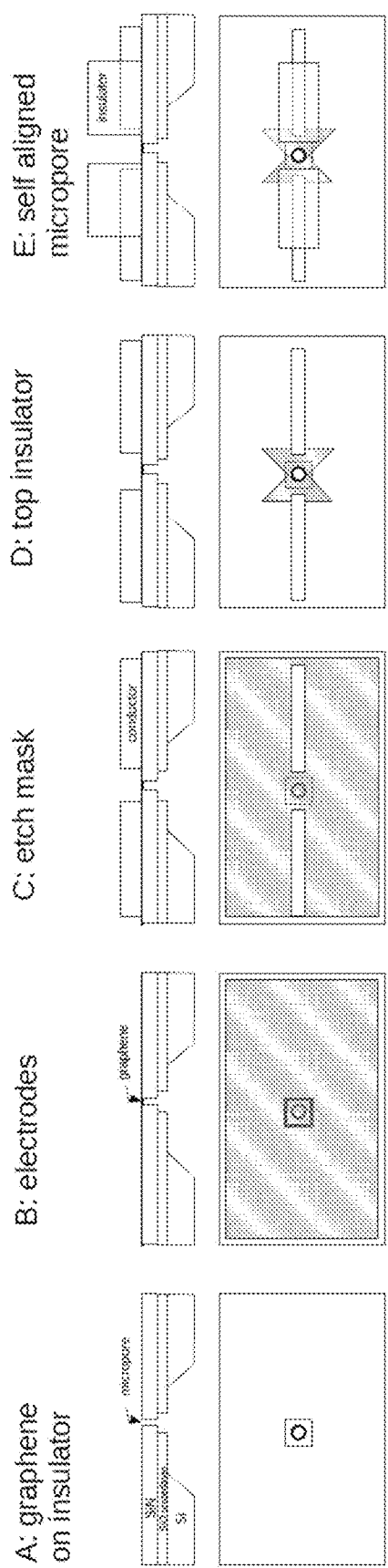
FIG. 3 shows A) graphene on insulator over supporting membrane. B) conducting electrodes. C) Patterned bow-tie shape in graphene membrane. D) top insulator covering the metal electrodes and the graphene. E) self-aligned hole in the top and bottom of the insulating layers sandwiching the graphene sheet.

Another contemplated design for the device fabrication is shown in FIG. 3. In this design, the support structure does not contain a micropore yet. The graphene is either 1) deposited on a previously existing insulating layer, or 2) positioned together with an insulating layer in a transfer process, or 3) grown on the insulating layer. The graphene is etched in bow-tie shape and covered with another insulating layer. Now, when the graphene is heated to create the nanogap, the insulating layer is ablated exactly over the nanogap area, thereby creating a micropore above and below the graphene nanogap. The micropore may also be fabricated with lithography techniques.

Specifically, FIG. 3 shows A) graphene on insulator over supporting membrane. B) conducting electrodes. C) Patterned bow-tie shape in graphene membrane. D) top insulator covering the metal electrodes and the graphene. E) self aligned hole in the top and bottom of the insulating layers sandwiching the graphene sheet.

Figure 4:
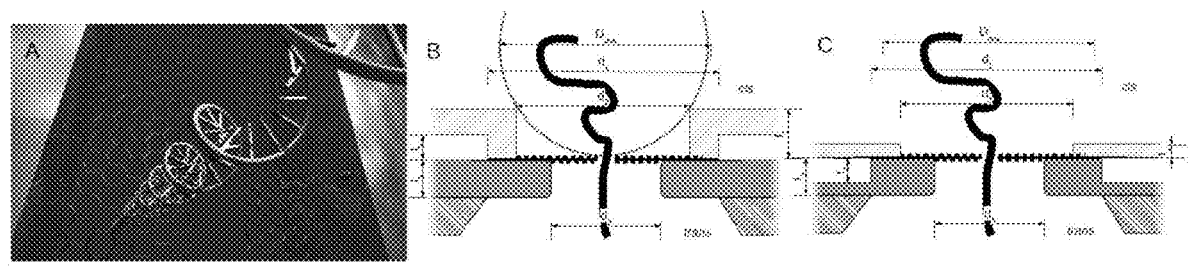
FIG. 4 shows A) 3D render of graphene sequencing device. Graphene (hexagonal lattice) is connected with metallic electrodes while a DNA molecule (helix) moves through it and the individual bases (cylindrical objects on helix) are probed electrically. B) Cross section of device. A micropore in a thin membrane with size dl is covered with a graphene sheet with self-assembled passivation layer. Metallic contacts are electrically connected to the graphene device and an insulating layer is placed over it with a hole with size d2. The DNA moves from the cis to trans side under an electrophoretic driving field. Before the DNA is captured and driven through the device, it occupies an approximately spherical space (dashes) with diameter Ddna. C) Alternative geometry with the metallic electrodes embedded into the membrane.

As disclosed herein, the functional components are layered in a way/process that enables the reliable assembly of contemplated devices. Contemplated devices comprise many layers that need to be fabricated on top of one another in careful manner, to prevent various undesirable effects, e.g. electrical shorts in the liquid between the metal electrodes, shorts across the membrane between the cis and trans side. [Add claim]: Contemplated devices may comprise the following layers: an insulating mechanical support substrate, a high dielectric strength insulating mechanical membrane, a thin mechanical membrane for supporting the graphene, a thin hydrophilic layer for good adhesion of graphene, a single or few-layer graphene piece, a layer of conducting electrodes, a passivation layer to insulate the graphene and electrodes from the solvents. The graphene layer is placed below the electrodes, on a flat substrate, to ensure adhesion during the deposition process. The layers are depicted in FIG. 4. In some of these embodiments, as mentioned throughout this work, some of the layers may be combined into one layer by utilizing specific materials and designs.

Specifically, FIG. 4 shows A) 3D render of graphene sequencing device. Graphene (hexagonal lattice) is connected with metallic electrodes while a DNA molecule (helix) moves through it and the individual bases (cylindrical objects on helix) are probed electrically. B) Cross section of device. A micropore in a thin membrane with size $d_1$ is covered with a graphene sheet with self-assembled passivation layer. Metallic contacts are electrically connected to the graphene device and an insulating layer is placed over it with a hole with size $d_2$. The DNA moves from the cis to trans side under an electrophoretic driving field. Before the DNA is captured and driven through the device, it occupies an approximately spherical space (dashes) with diameter $D_{dna}$. C) Alternative geometry with the metallic electrodes embedded into the membrane.

In one contemplated embodiment, for example, a graphene sheet is covering an approximately 500 nm micropore in a Si/SiO2 wafer and the wafer is mounted in a PDMS fluid cell with integrated Ag/AgCl electrodes for ion current measurement as well as contacts to the Au electrodes for transverse conductance measurement.

A significant advantage, as mentioned earlier, to contemplated embodiments is that the macromolecule translocation device is accessible to liquids—while insulating the electronics—by geometrically biasing the nanogap formation over liquid accessible parts of the device. A crucial component of the device is that the nanogap needs to be accessible to liquids from the top, cis, and bottom, trans, sides while being insulated further away and mechanically supported. Therefore, the device requires d3<d1.

One advantage of the processes and methods disclosed herein is that the size of the thinnest mechanically cantilevered components can be controlled in order to inhibit the mechanical fluctuations of contemplated devices. Specifically, Movement of the half edge of the graphene nanogap device is limited to minimize mechanical motion which would inhibit the spatial resolution of the device. If this section is made too small, the fabrication of the device is cost prohibitive. The optimum size of the freely suspended section ($d_3$ in FIG. 4) that we have determined is therefore a crucial parameter. The fluctuations are $\delta x = \delta 0 d_3^{3/2}$ so with a maximum tolerable level of fluctuations $\delta M$ the maximum size the device requires is $d3 < (\delta M/\delta 0)^{2/3}$.

Figure 5:
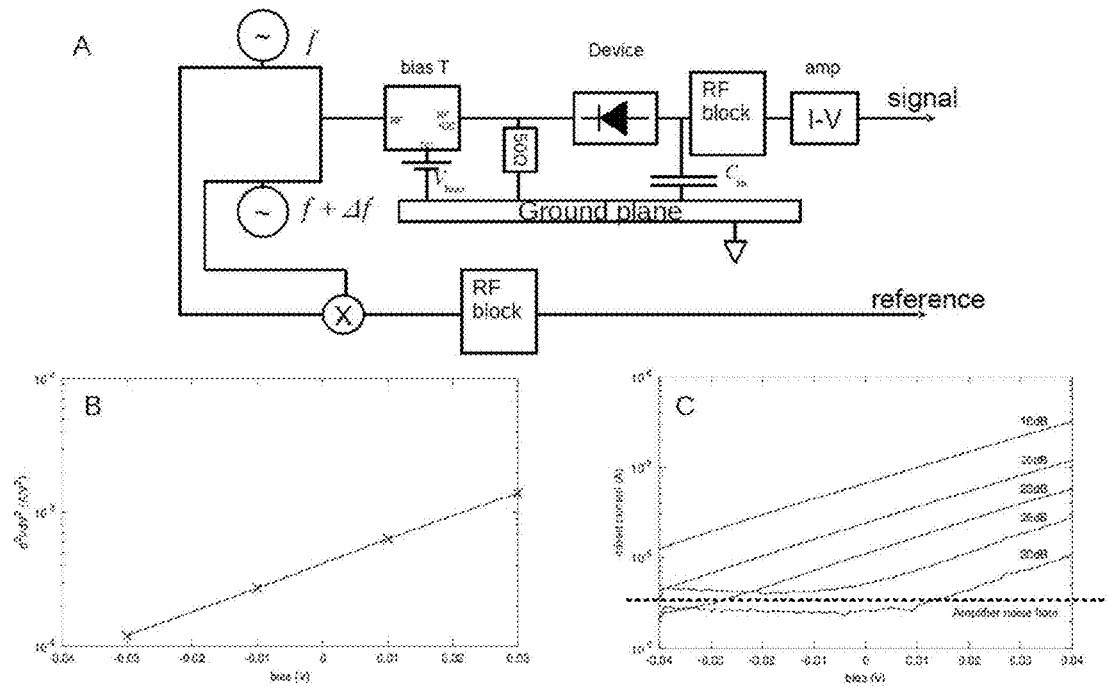
FIG. 5 shows A) circuit diagram of using the nonlinear conductance of the device as a mixer. Two sources send a signal to a nonlinear device that is biased with an independent bias voltage Vbias. The mixed signal is low bass filtered and sent to a current amplifier ("I-V"). A separate reference is used to compare the signal to. B) Nonlinear characteristic of test device as a function of Vbias. C) Mixed signal as a function of Vbias, in agreement with the nonlinear signature.

The high-impedance nature of the molecule-graphene device makes reading a signal at high frequencies very challenging, and the bandwidth is limited by the parasitic capacitance. Impedance matching techniques may be utilized but become practically impossible once the impedance of the device exceeds 50Ω by a few orders of magnitude. We have developed a mixing technique that relies on the non-linear I(V) characteristic. Two high frequency sources with frequency f and f+Δf are both sent to the device and the nonlinear nature of the device yields signals at 2f+Δf and Δf. The signal at Δf is recorded and is extracted with a custom high frequency current amplifier. Higher order components are measured to determine the molecule properties in a manner that does not depend on the local nanogap width. The circuit diagram, nonlinear characteristic and mixing characteristics of a nonlinear device are shown in FIG. 5. The device requires recording two of the coefficients of the Taylor expansion of the device I(V), i.e.

$$I(V) = I_0 + \frac{\partial I}{\partial V} V + \frac{1}{2}\frac{\partial^2 I}{\partial V^2} V^2 + \frac{1}{6}\frac{\partial^3 I}{\partial V^3} V^3 + ... \quad (1)$$

Higher order moments can be read with either two sources at different power levels, or reading higher order modulations, ie. reading the signal at 2Δf or 3Δf. The clean delivery of the high frequency signal to the device requires a 50Ω termination close to the device.

Specifically, FIG. 5 shows A) circuit diagram of using the nonlinear conductance of the device as a mixer. Two sources send a signal to a nonlinear device that is biased with an independent bias voltage Vbias. The mixed signal is low bass filtered and sent to a current amplifier ("I-V"). A separate reference is used to compare the signal to. B) Nonlinear characteristic of test device as a function of Vbias. C) Mixed signal as a function of Vbias, in agreement with the nonlinear signature.

Specifically, contemplated molecule or macromolecule translocation devices are nonlinear conductors and can utilize a mixing technique, wherein the mixing technique comprises: providing a first high frequency source having a frequency f to the device, providing a second high frequency source having a frequency f+Δf to the device, mixing the first high frequency source frequency with the second high frequency source frequency to yield a first signal at 2f+Δf and a second signal at xΔf, wherein x is an integer.

Contemplated devices are tightly integrated with a shielding ground plane, and the device is placed very close to a high-speed preamplifier stage (FIG. 5). The crucial parameter here is the proximity of the amplifier to the device. This distance is minimized to limit parasitic impedance Cin on the input of the amplifier which would limit its bandwidth, gain, and noise. The device requires Cin<Cmax, where Cmax is the highest tolerable input capacitance, due to e.g. injected current noise to the device. Ultimately, this process uses a high-speed amplifier to work as an instrument for the required low noise measurement.

These contemplated devices and the methods and processes that are disclosed herein to produce these devices are designed to ultimately allow the translocation and sequencing/identification of macromolecules. Contemplated devices control the molecules and query them in a linear fashion by chemically, thermally, and electrostatically keeping them separated and in a linear form.

Specifically, sequencing a single-stranded molecule with this device requires driving it through the device in a linear fashion. ssDNA has been sent through nanopores before, but the length of these segments is limited to several thousand bases (Kowalczyk et al., 2010), well below the million bases that we are aiming for. This is usually due to ssDNA binding to itself and forming a secondary structure that prohibits translocation through a nanopore when the molecule is much larger than the persistence length $L_b = EI/k_B T$. Note that Oxford's nanopore platform reads Mb long segments but uses an enzyme to cleave the dsDNA right at the nanopore entrance. We do not use enzymes in the approach here, since they introduce a restrictive rate limit and limit the environmental tolerance and shelf life of the device. RNA also has a rich secondary/tertiary structure, which would also be inhibited in the same manner. We have developed a protocol for inhibition of secondary structure that uses a combination of chemical melting, maximizing the electrostatic self repulsion, and thermal melting.

Figure 6:
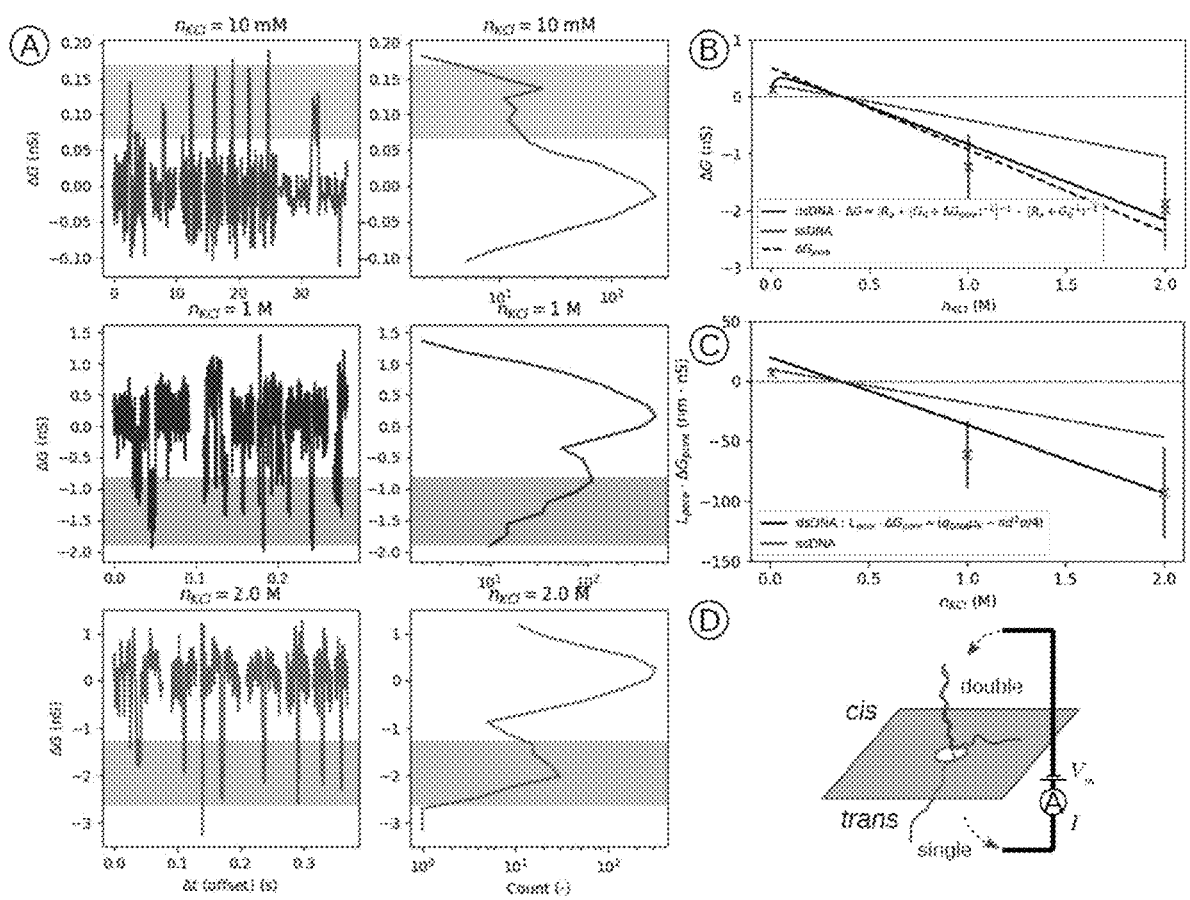
FIG. 6 shows A) Unzipping of high-molecular-weight DNA through SiN nanopores. A) Left: Subset of ΔG for events at nKCl=0.010, 1, and 2 M. Right: Histogram of all event current traces for corresponding conditions in left panel with secondary peak width (shaded). B) Expected mean of ΔG values of ssDNA (blue), dsDNA, and Eq. 2 (dashed) vs. nKCl. C) Expected mean of Lpore ΔGpore for ssDNA and dsDNA (black) vs. nKCl. The 2M and 1M align with dsDNA and the 10 mM aligns with ssDNA. D) Diagram of dsDNA unzipping, as it moves through a nanopore in a membrane from the cis to trans side driven by a transmembrane potential Vm while monitoring the current I.

The data in FIG. 6 shows free running translocation without secondary structures of ssDNA that is an order of magnitude longer than reported before. This is accomplished by in situ melting and unzipping of long, high molecular weight DNA. At varying salt concentration, we directly compare the translocation conductance and speeds between SiN and graphene nanopores at sub-10 nm pore diameters.

Specifically, FIG. 6 shows A) Unzipping of high-molecular-weight DNA through SiN nanopores. A) Left: Subset of ΔG for events at nKCl=0.010, 1, and 2 M. Right: Histogram of all event current traces for corresponding conditions in left panel with secondary peak width (shaded). B) Expected mean of ΔG values of ssDNA (blue), dsDNA, and Eq. 2 (dashed) vs. nKCl. C) Expected mean of Lpore ΔGpore for ssDNA and dsDNA (black) vs. nKCl. The 2M and 1M align with dsDNA and the 10 mM aligns with ssDNA. D) Diagram of dsDNA unzipping, as it moves through a nanopore in a membrane from the cis to trans side driven by a transmembrane potential Vm while monitoring the current I.

We observe a series of short changes in the ion conductance ΔG across the nanopore (FIG. 6) every time a DNA molecule translocates through the pore (Dekker, 2007). To ensure these fluctuations are well separated from the baseline current Ibg and display a distinctive peak in the ion current histogram, we limit the passage of folded molecules by fabricating relatively small nanopores, d=4 to 7 nm.

At high nKCl, we normally find ΔG<0 because it is dominated by the exclusion of ions from the nanopores.

Conversely at low nKCl, ΔG>0, since counterion current from the DNA backbone dominates (Smeets et al., 2006). Both effects are described by:

$$\Delta G_{pore} = \left( \underbrace{-\frac{\pi}{4}d_{DNA}^2 \sigma' \mu_R}_{\text{exclusion}} + \underbrace{\mu_K^* q_{L,DNA}^*}_{\text{backbone}} \right) / L_{pore}. \quad (2)$$

The initial value of the nanopore diameter d was determined from the open pore conductance G using the bare pore conductance $G_0$ and access resistance $R_a$ (Smeets et al., 2006; Hall, 1975):

$$G = (G_0^{-1} + R_a)^{-1} \quad (3)$$

$$G_0 = \underbrace{\frac{\pi d^2}{4L_{pore}}(\mu_K + \mu_{Cl})en_{KCl}}_{=\sigma} + \frac{\pi \mu_K \sigma_q d}{L_{pore}}$$

$$R_a = \frac{1}{\sigma d}$$

Note that σq is surface charge density while nKCl conductivity is σ. The pore diameter d and depth $L_{pore}$ were determined self consistently using G(nKCl=2M) and ΔG(nKCl=2M). "d" is the real root of the cubic equation:

$$I_3 d^3 + I_1 d + I_0 = 0$$

Where:

$$G_2 \equiv G(n_{KCl} = 2M)$$

$$\Delta G_2 \equiv \Delta G(n_{KCl} = 2M)$$

$$I_3 = \pi \sigma / 4 (1/\Delta G_2 + G_2) - 1/G_2)$$

$$I_1 \equiv [-d_{DNA}^2 \pi \sigma / 4 + \mu^* q_{DNA}]/(\Delta G_2 + G_2)\lambda$$

$$I_0 \equiv [d_{DNA}^2 \pi \sigma / 4 - \mu^* q_{DNA}]/\sigma$$

It follows:

$$d = (0.38157 x / I_3 - 0.87358 I_1 / x)\lambda$$

Where:

$$x = (1.7321 \sqrt{27 I_3^4 I_1^2 + 4 I_3^3 I_1^3} - 9 I_3^2 I_0)^{1/3}$$

The scale parameter $\lambda = 10^{-9}$ is used to keep $I_3$, $I_1$, and $I_0$ of similar magnitude. The depth is then:

$$L_{pore} = \pi \sigma d^2 / 4 (1/G_2 - 1/(\sigma d))$$

This calibration works well for SiN nanopores, but it is expected to be an overestimate of d and $L_{pore}$ for graphene nanopores because of the non-uniformity of j as described.

The values for ΔG at low nKCl are much lower than Eq. 2 describes. We argue that in a low nKCl regime, the effect of access resistance Ra must be taken into account. When the pore is open, Ra and $1/G_0$ constitute a voltage divider, whereas when DNA is inside the pore, Ra and $1/(G_0+\Delta G_{pore})$ constitutes one. If d<<Lpore at high $n_{KCl}$, most of the voltage drops across the pore and ΔG follows Eq. 2. However, at low $n_{KCl}$ the geometric dependence of $\Delta G_{pore}$ changes and the condition d<<$L_{pore}$ no longer guarantees Ra<<(G0+$\Delta G_{pore}$)$^{-1}$. Consequently, the quantity actually measured is:

$$\Delta G = [R_a + (G_0 + \Delta G_{pore})^{-1}]^{-1} - (R_a + G_0^{-1})^{-1} \quad (4)$$

as shown in FIG. 6. We extract ΔGpore using the inverse of Eq. 4, causing the ssDNA and dsDNA curves at low nKCl to separate and observe a distinct grouping of ΔGpore on the ssDNA curves. We therefore conclude that we are unzipping dsDNA at the nanopore entrance and drive it through the nanopore free from secondary structure, due to the much longer persistence length at low nKCl and the much-reduced screening of the negatively charged backbone at low ionic strength.

Contemplated embodiments disclosed herein allow for the extraction of the real time clock of molecules by monitoring the high frequency pulsing behavior of the molecule as it goes through the device. The single-base resolution that is expected for this type of device in principle allows one to extract the rate of translocation as the molecule is going through the gap through a series of peaks. This implies that even if the speed of translocation is not uniform, as expected, the sequence can still be extracted. This well-defined clock is also the enabling feature to sequence homopolymeric sequences. The device therefore uses the real time clock of the molecule signal to extract the instantaneous speed and map that to a position along the molecule length.

Additionally, some contemplated planar devices allow for querying long molecules without an entropic barrier. Our aim of being able to read the base sequence of >1 Mb long molecules requires that there is no entropic barrier to molecules on the cis side. We have designed this side to be as planar as possible. The largest out-of-plane constriction on the cis side is constituted by the electrodes and their passivation layer (FIG. 4) that define an opening with size $d_2$ and depth t1. The molecules that we are driving through the device occupies a space with diameter $D_{dna} = 2R_g$ where $R_g$ is the radius of gyration of the molecule. A contemplated device being used in this way requires that:

$$t_1 < \frac{1}{2}(D_{dna} - \sqrt{D_{dna}^2 - d_2^2})$$

This requirement may also be met by immersion of the metallic electrodes into the membrane, which then has the same criterion for the relation between $t_1$, $D_{DNA}$, and $d_2$.

EXAMPLES

Example 1: Demonstration of Single-Base Resolution

Figure 7:
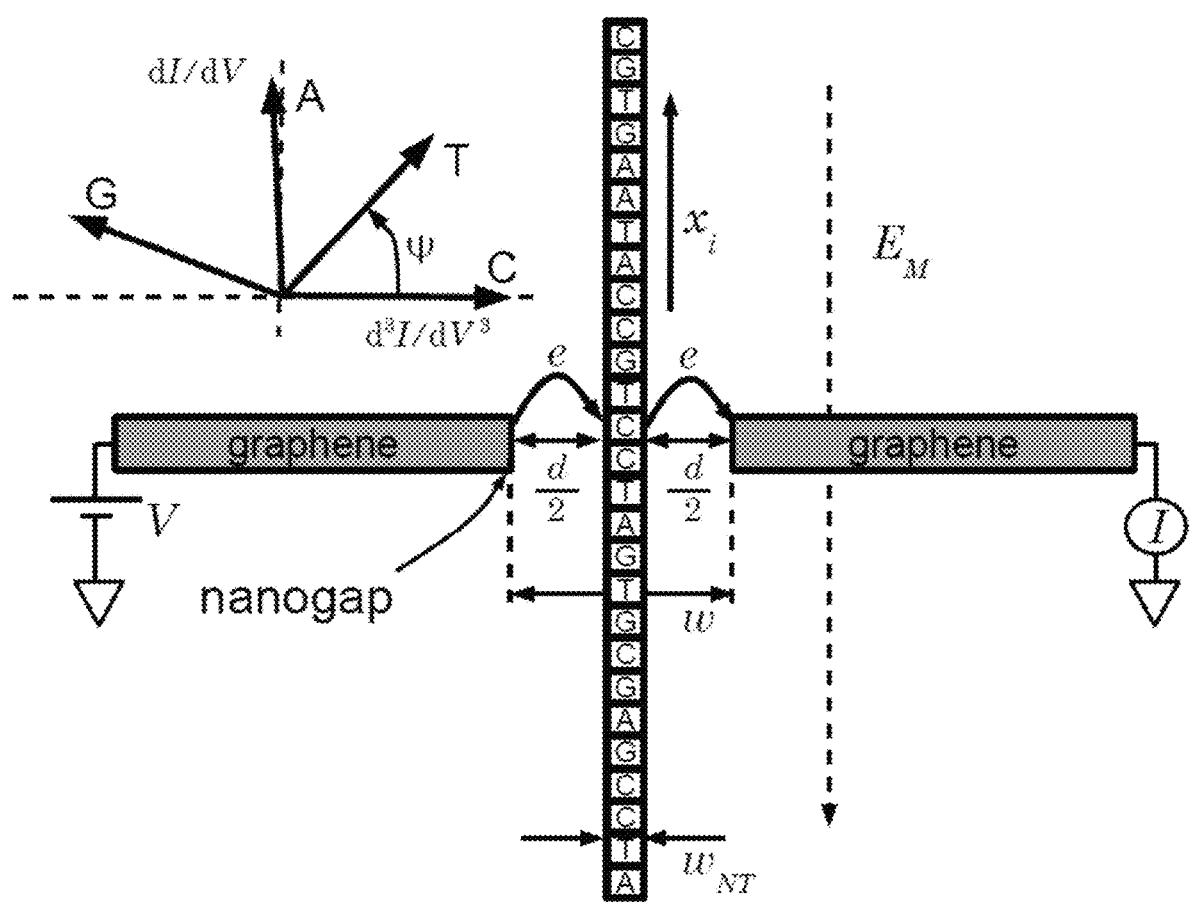
FIG. 7 shows the effective tunnel distance of a contemplated embodiment.

To demonstrate the single-base resolution of the proposed graphene nanogap sequencing technique, a numerical simulation is presented here based on the first-principles results of He et al. Since electrical transport through the bases of the DNA molecule occurs through resonant tunneling, the current depends on distance as:

$$I(V) = I_0^X(V) e^{-2\kappa d_t}$$

where $d_t$ is the effective tunnel distance, as shown in FIG. 7, $I_0^X(V)$ is a voltage-dependent prefactor that depends on the base type X={A, T, C, G} (Table 1), $\kappa = (2_{m\varphi})^{1/2} \hbar = 1.1 \times 10^{10}$ m$^{-1}$ is the decay constant, m=9.1×10$^{-31}$ kg is the electron mass, φ=4.66 eV is the graphene workfunction, and $\hbar = 6.63 \times 10^{-34}/2\pi$ J s is the Dirac constant. For applied voltages V<<φ/e, the effective tunneling distance does not depend on V.

TABLE 1

Table of Angles and Derivatives for the Different Base Types, Derived from He et al.[27]

|  | A | T | C | G |
|---|---|---|---|---|
| $\alpha = dI/dV$ (nS) | 26.9 | 10.4 | −0.218 | 6.45 |
| $\beta = d^3I/dV^3$ (nS) | −1.22 | 9.10 | 21.0 | −15.9 |
| $\psi$ (deg) | 92.6 | 48.7 | −0.60 | 157.9 |

Figure 8:
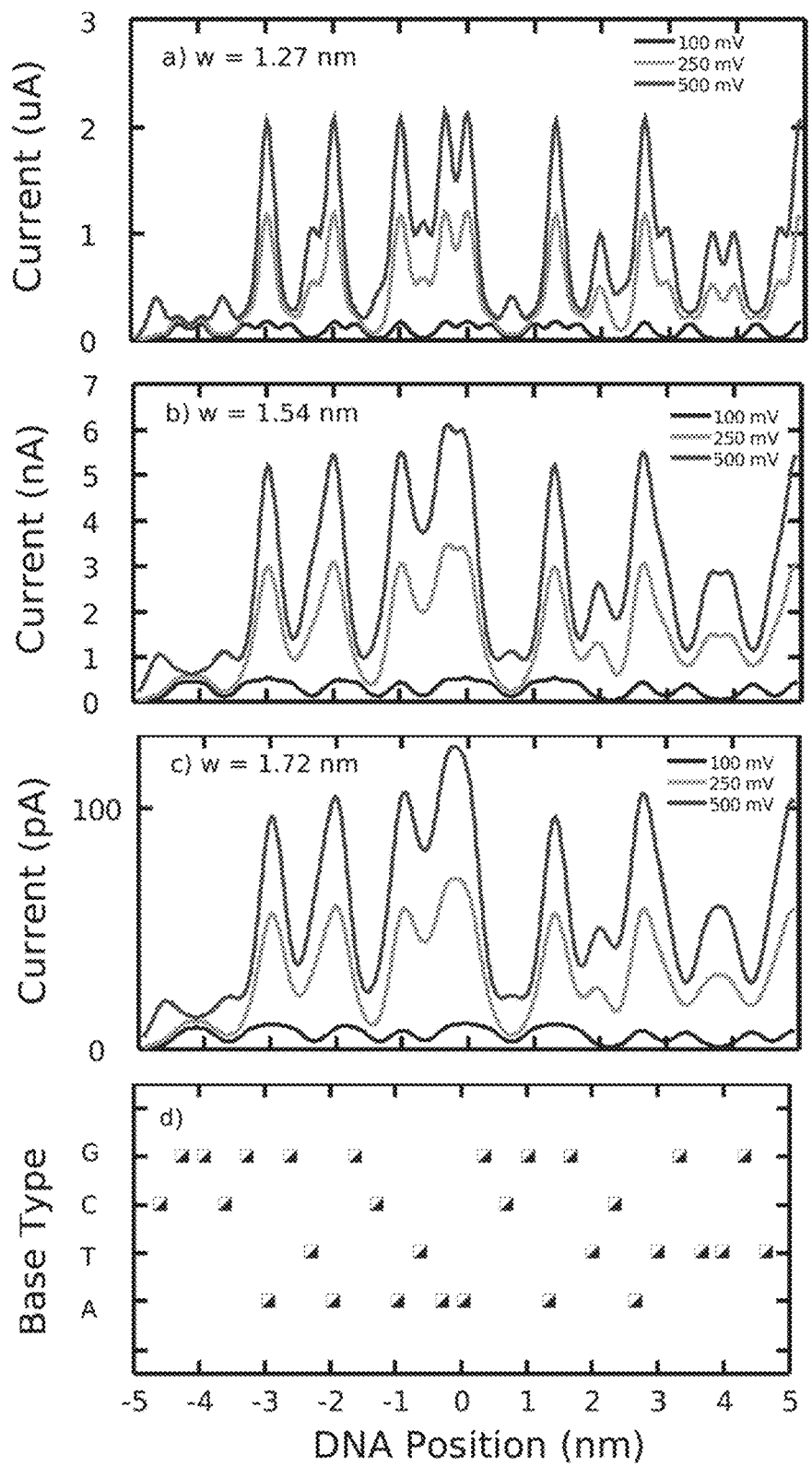
FIG. 8 shows the current across the graphene nanogap while a single-stranded DNA molecule translocates through it for three different gap widths w and bias voltage levels as indicated. (d) For this simulation, a random sequence of CGG CGA GTA GCA TAA GCG AGT CAT GTT GT was used.

A random set of N bases $X_i=\{A, T, C, G\}$ is chosen with distances $x_i$ along the backbone. The bases are 0.33 nm apart. The current is calculated as the sum of the currents due to all bases with an effective tunnel distance $d_r^2=d^2+(x_i-x_0)^2$ $$I(V, x_0) = \sum_{i=1}^{N} I_0^{X_1}(V) e^{-2\kappa\sqrt{d^2+(x_i-x_0)^2}} \quad (1)$$

where $x_0$ is the position of the center of the DNA molecule with respect to the center of the nanogap. The translocation process is simulated by varying $x_0$. The results presented in FIG. 8 show a series of current peaks that correspond to the individual nucleotides. It demonstrates that the individual bases can be resolved with this technique. Specifically, FIG. 8 shows the current across the graphene nanogap while a single-stranded DNA molecule translocates through it for three different gap widths w and bias voltage levels as indicated. (d) For this simulation, a random sequence of CGG CGA GTA GCA TAA GCG AGT CAT GTT GT was used.

To demonstrate how a change in nanogap width affects the current, the simulation is performed for different nanogap widths $w=d+w_{NT}$, where $w_{NT}\approx 1$ nm is the single-nucleotide size (FIG. 8). As the nanogap becomes wider, the current peaks become broader. Equation 1 can be rewritten as a convolution integral to illustrate this broadening, as:

$$I(V, x_0) = \int_{-\infty}^{\infty} B(x)W(x_0-x)dx \quad (2)$$

$$B(x) \equiv \sum_{i=1}^{N} I_0^{X_1}(V)\delta(x-x_i)$$

$$W(x) \equiv \exp\left(-2\kappa\sqrt{d^2+x^2}\right)$$

where B(x) is the function that describes the bases' positions and their current and W(x) is a peak function that describes the overlap between the DNA and graphene electron wave functions. It has a width $\delta x=(1/\kappa^2+4d/\kappa)^{1/2}$ at 1/e of its height. The minimum width, and therefore the highest degree of spatial resolution for transverse conductance measurements, is $1/\kappa=0.09$ nm, and it increases with increasing nanogap width d, which explains the observed broadening. The form used here is based on the assumption that the wave functions have a symmetry that causes the decay constant not to change when the nucleotide is moving through the nanogap, i.e., when $x-x_i$ is varied. It is expected that because these wave functions do not have this symmetry, W(x) will be more articulated with a resulting higher spatial resolution than the conservative results presented here. The actual broadening function W(x) as well as the angles $\psi x$ can be determined experimentally by measuring poly-A, -T, -C, and -G consecutively. The work function in water is typically 1.1-1.4 eV lower than that in vacuum, which changes $\kappa$ to 9.4×10⁹ m⁻¹. This means that the peaks will be wider in water by ~8% for tunneling distances $d \gg \frac{1}{4}\kappa$ and ~16% for $d \ll \frac{1}{4}\kappa$.

In addition to the current peaks becoming wider, the overall current decreases exponentially with the nanogap width. A technique is required that will distinguish current changes due to base variations from changes due to nanogap-width variations. Herein, the idea is to use the nonlinear current-voltage characteristic to allow for base characterization independent of the nanogap width.

Figure 9:
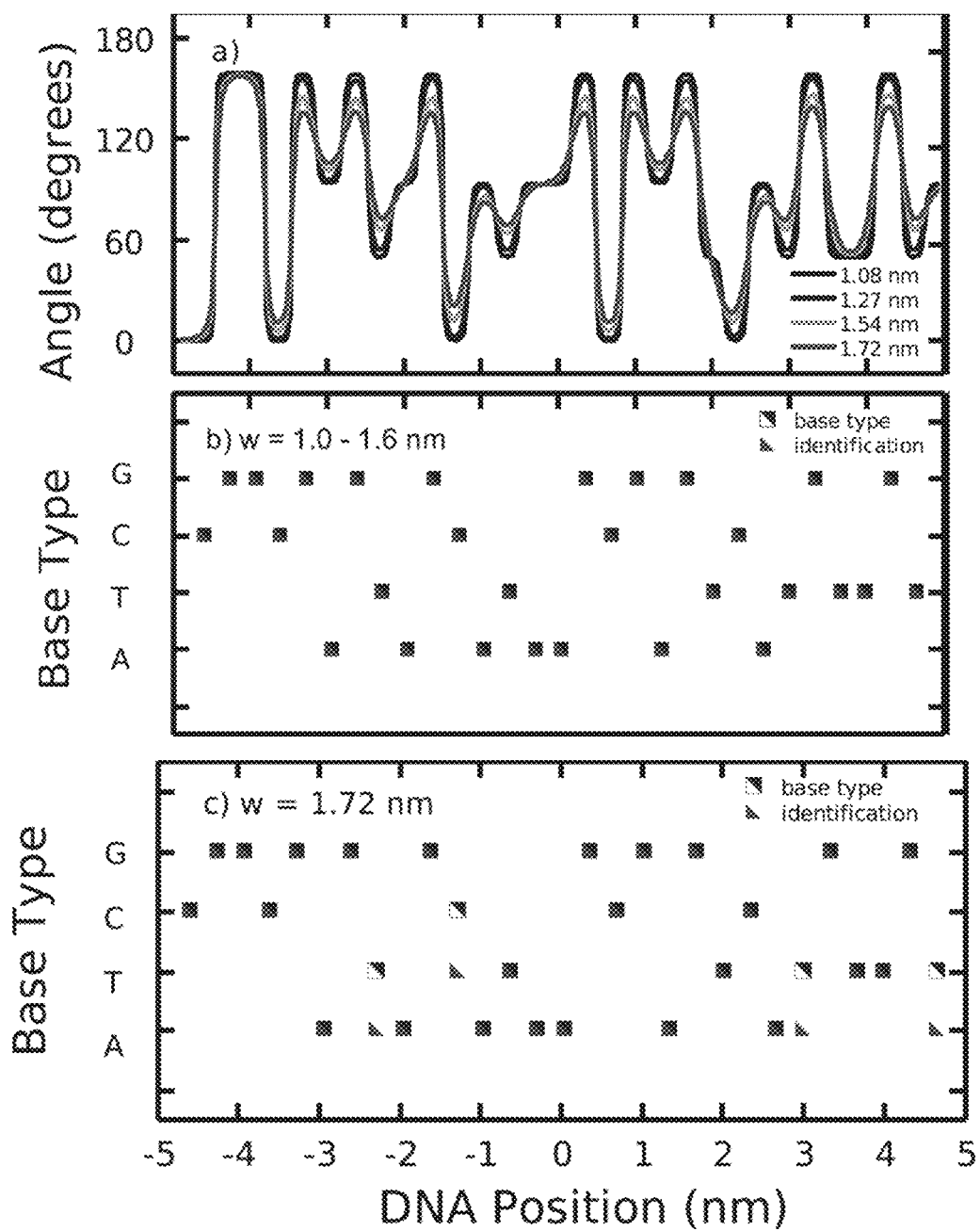
FIG. 9 shows the angles ψ for w=1.08, 1.27, 1.54, 1.72 nm. When the nucleotide is at the center of the nanogap, the angle becomes stable. (b) The angle is used to determine the base type as described in the text (triangles, base type; triangles, deduced base type from ψ). For w=1.1-1.6 nm, the base type is deduced accurately. (c) When w=1.7 nm, the overlapping current peaks cause misidentification.

Because the current depends exponentially on distance, the first, $\alpha \equiv dI/dV$, and third derivative, $\beta \equiv d^3I/dV^3$, depend exponentially on distance in the same manner. Therefore, $\psi \equiv \text{Arg}(\beta+i\alpha)$ is distance independent. The simulation is performed in the same manner as above, now varying the nanogap width and calculating $\alpha$ and $\beta$. The angle $\psi$ is plotted as the DNA moves through the nanogap (FIG. 9). When the bases are aligned with the nanogap, the angle becomes stable and its value is approximately the same for all nanogap widths. It is then used to determine the base type, as plotted in FIG. 9. The triangles indicate the actual base type while the red triangle indicates what the deduced base type is based on $\psi$.

Specifically, FIG. 9 shows the angles $\psi$ for w=1.08, 1.27, 1.54, 1.72 nm. When the nucleotide is at the center of the nanogap, the angle becomes stable. (b) The angle is used to determine the base type as described in the text (blue triangles, base type; red triangles, deduced base type from $\psi$). For w=1.1-1.6 nm, the base type is deduced accurately. (c) When w=1.7 nm, the overlapping current peaks cause misidentification.

Figure 10:
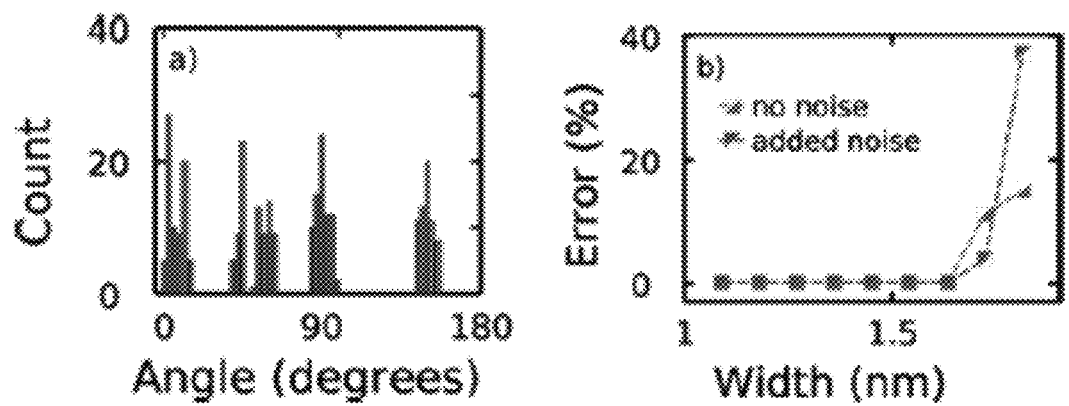
FIG. 10 shows (a) Histogram of recorded angles ψ when the nucleotide is in the center of the nanogap with width w=1.54 nm. Four well-separated peaks show that the angle can be used to identify the base type. (b) Sequence error rate with and without added Johnson-Nyquist noise.

The histogram of recorded angles is presented in FIG. 10 and shows four well-separated peaks due to the different base types. It is clear that this method can be used to sequence an individual DNA molecule although nanogap-width variations cause the current to vary by more than 5 orders of magnitude. Specifically, FIG. 10 shows (a) Histogram of recorded angles $\psi$ when the nucleotide is in the center of the nanogap with width w=1.54 nm. Four well separated peaks show that the angle can be used to identify the base type. (b) Sequence error rate with and without added Johnson-Nyquist noise.

When the nanogap is equal to 1.7 nm, the peaks become so broad that currents due to adjacent bases start to influence the current due to the base in the center of the nanogap. This leads to a misidentification of the base type (FIG. 9). This misidentification can be remedied by deconvolving the recorded current using eq 2. This broadening is the prime source of sequencing errors, and the rate at which it occurs is indicated in FIG. 10.

Current fluctuations will lower the fidelity $f$ with which $dI/dV, d^3I/dV^3$, and $\psi$ can be measured. To simulate this, Johnson-Nyquist current noise with a magnitude of $\delta I=(4k_BTIB/V)^{1/2}$ is added to the current signal, where $k_B$ is Boltzmann's constant, T is the absolute temperature, B=1 MHz is the measurement bandwidth, and V is the applied voltage. These current fluctuations alter the sequencing error rate slightly (FIG. 10). Initially, the errors are due to broadening of the current peaks, but later the current fluctuations become dominant. The error rate can be evaluated analytically as well. The current noise amplitude causes fluctuations in $\alpha$ and $\beta$ that are not correlated when they are measured at different frequencies with a lock-in technique, and they in turn cause fluctuations $\delta\psi$ in the measured angle $\psi$. For a high-fidelity determination of the base type, we require that $\delta\psi$ is much smaller than the smallest difference between the values $\psi$, which for the simulation presented above is $\Delta\Psi\text{min}=44°$ between A and T. The root mean square fluctuation amplitude in the angle is equal to:

$$\delta\psi = \arctan\left(\frac{\delta I}{I}\right) = \arctan\left(\sqrt{\frac{4k_BTB}{IV}}\right) \quad (3)$$

which leads to a sequencing error rate 1–f for the misidentification of A as T and vice versa of:

$$1 - f = \frac{1}{2}\left(1 + \text{erf}\left(\frac{\psi}{\sqrt{2}\,\delta\psi}\right)\right) \quad (4)$$

where $\text{erf}(x) \equiv \int_0^x \exp(-t^2)\,dt$ is the error function. Another source of fluctuations is thermal vibrations of the graphene membrane. The membrane is easily bent in the direction perpendicular to the membrane plane owing to its single-atom thickness. Thermal vibrations of this bending mode lead to a stochastic variation of the position of the nanogap with respect to the DNA longitudinal axis, and it limits the longitudinal resolution with which the base's transverse conductance can be measured. Extrapolating using the scaling behavior $\delta \times M \propto (L/t)^{3/2}$ from recent studies of spring constant and mechanical resonator measurements of few-sheet graphene membranes, the thermal noise amplitude can be estimated to be 0.16 nm for a 0.6 nm thick and 500 nm long membrane. This is smaller than the 0.3 nm distance between bases, which means that single-base resolution will be possible despite these mechanical vibrations.

Brownian motion of the ssDNA molecule will lead to a stochastic variation of the position of the nucleotides $\delta x_0$ inside the nanogap. An upper limit to the magnitude of this effect can be estimated from the free diffusion of DNA when it is not inside the nanogap, as $\delta x_0 \sim (4D\tau)^{1/2}$, where $D=1.0 \times 10^{-8}$ cm$^2$/s is the free diffusion coefficient, 56 and $\tau \sim 1$ μs is the average time a nucleotide spends in the nanogap. This upper limit is $\delta x_0 \sim 2$ nm, which is larger than the base-to-base distance. However, the diffusion coefficient is most likely much smaller in the confined nanogap geometry. In addition, it may be made smaller by functionalizing the nanogap. Finally, driving the DNA through the nanogap more quickly will reduce $\tau$ and, consequently, $\delta x_0$ even further.

To prevent a parasitic current pathway from the graphene surface through the ionic solvent that bypasses the nanogap, the graphene may be covered with a self-assembled monolayer. This will also improve the wetting properties of the graphene surface, limit electrochemical reactions of the graphene surface in contact with the solvent, and prevent adhesion of the DNA to the graphene surface. Residual parasitic current between the unpassivated carbon atoms at the edge of the nanogap will cause an extra contribution to the current and its first derivate dI/dV. This offset can be calibrated before and after the DNA has translocated through the nanogap and subtracted to compensate for this effect.

It has been calculated that geometric fluctuations of the nucleotides while they are in the nanogap can lead to large fluctuations in the transverse conductance, limiting how well nucleotides can be distinguished. Rotational fluctuations can be caused by (1) rotation of the bases around the bond to the backbone $\delta\theta$, and (2) overall rotation of the DNA molecule inside the nanogap $\theta$. Due to the fact that the persistence length of the DNA molecule is much larger than the base-to-base distance, it can be expected that the second effect will lead to a similar fractional change in conductance for consecutive bases as the molecule translocates through the nanogap. The presence of this effect and how it changes the current can therefore be deduced from a comparison of $\psi$ for consecutive bases. The first effect will lead to a stochastic variation of the angle $\delta\theta$ around the average value $\theta$. A detailed study of how this changes the nonlinear conductance and $\psi$ is the subject of other examples.

These conductance fluctuations may be reduced by stabilizing the nucleotides while they are in the nanogap, e.g., by functionalizing the nanogap with cytosine or by the applied bias voltage. As an alternative to the transverse conductance technique proposed here, the presented device can also be used to directly detect voltage fluctuations due to the local and unique dipole moments of the bases. This capacitive detection approach is not preferred, however, due to its reliance on the relatively long-range capacitive interaction, possibly limiting the spatial resolution with which individual bases can be resolved. For further studies of the proposed technology, the contribution of counterions and the unique density of states of graphene need to be taken into account. In addition, doping due to adsorbed water molecules on the graphene membrane and its reduction in the absence of an underlying SiO2 substrate needs to be considered.

Example 2: In Situ Unzipping of Long, High Molecular Weight DNA in Solid State Nanopores Nanopores are an established paradigm in genome sequencing technology, with remarkable advances still being made today. All efforts continually address the challenges associated with rapid, accurate, high-throughput, and low-cost detection, particularly with long-read length DNA. We report on the in situ melting and unzipping of long, high molecular weight DNA. At varying salt concentration, we directly compare the translocation conductance and speeds between SiN and graphene nanopores at sub-10 nm pore diameters. We observe the force-induced unzipping of dsDNA at higher salt concentrations than previously reported in literature. We observe free running translocation without secondary structures of ssDNA that is an order of magnitude longer than reported before. We hypothesize that the frayed single strands at the molecule's end get captured with a higher likelihood than both ends together. In understanding this phenomenon for long-read lengths, we continue to address the challenges revolving around future generations of sequencing technology.

Genome sequencing is an advancing field with applications in clinical diagnostics. However, the challenges of providing accurate identification of longer DNA molecules at low cost are still developing. While detection of long DNA molecules is established, the identification of its individual nucleotides presents its own set of challenges. By separating the hydrogen bonds between the two strands, individual nucleotides are made directly measurable. However, identification is hindered from the formation of secondary structures, where the single-stranded DNA sticks to itself. Previous studies only included short DNA molecules. We report in situ force-induced unzipping and translocation of long DNA without secondary structures almost an order of magnitude longer than reported before. Our findings present new experimental conditions and insights that progress the field towards high accuracy sequencing of individual long molecules.

A. Materials

Solid SiN membranes were acquired from Norcada Inc (NX5004Z-60O). They consist of a 5×5 mm$^2$ Si frame with thickness of 200 µm, a (20-30 µm)² membrane with thickness 12 nm, and a 60 nm thick underlayer of SiO₂. SiN membranes with a micropore for graphene studies were acquired from Norcada Inc (custom order). They either had a 5×5 mm² or 3.5×5 mm² Si frame with 200 µm thickness, a 50 µm membrane with thickness of 200 nm or 50 nm, respectively, and a 60 nm thick underlayer of SiO and a 5 nm overlayer of SiO for improved adhesion to graphene. Micropore diameters ranged from 0.5-2 µm.

B. Device Fabrication

Figure 11:
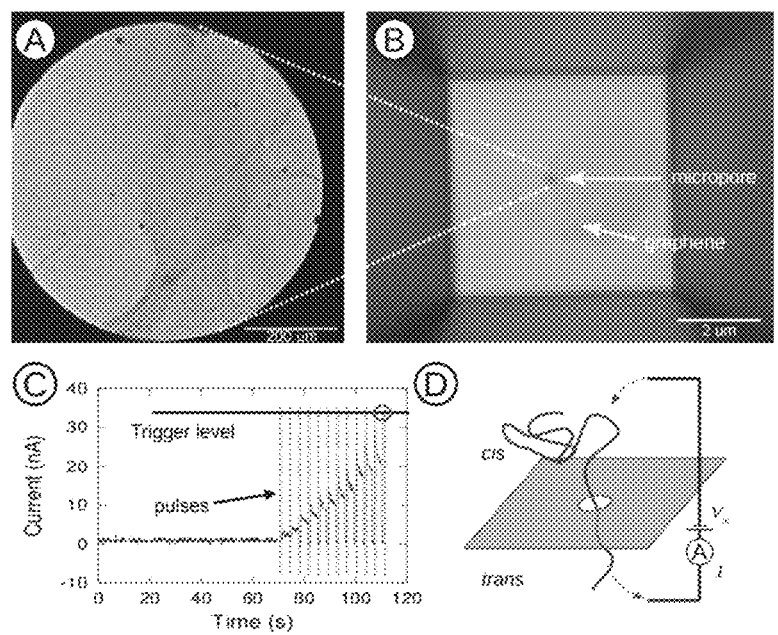
FIG. 11 shows fabrication of nanopores and DNA translocation procedure. A) Transmission Electron Micrograph of suspended graphene membrane over micropore. B) Optical image of graphene membrane over micropore. C) Nanopore fabrication procedure. For graphene nanopore, a pulsing procedure was used, which was terminated at reaching a predetermined trigger level. For SiN membranes, a constant voltage procedure was used (not shown). D) A transmembrane voltage Vm is applied and the ion current I (dashed) is measured as DNA (green) translocates through a nanopore from the cis to trans side.

Graphene samples, shown in FIG. 11, were made from mechanically exfoliated 5-10 mm size natural graphite (NGS Naturgraphit GmbH) flakes with Blue Nitto tape (Nitto Denko, SPV 224LB-PE). Graphite flakes were deposited on 300 nm SiO₂/500 µm Si wafers that were previously cleaned in separate ultrasonic baths of Acetone (PHARMCO-AAPER), IPA (99%, PHARMCO-AAPER), de-ionized Water, and dipped in a 6:1 Buffered Oxide Etch (HF, JT.Baker 1178-03). Graphene flakes were identified with an optical microscope (Meiji MT7530 BF/DF), with thicknesses determined by optical contrast using a calibration curve obtained with Atomic Force Microscopy (Pacific Nanotech Dual Scan).

Specifically, FIG. 11 shows fabrication of nanopores and DNA translocation procedure. A) Transmission Electron Micrograph of suspended graphene membrane over micropore. B) Optical image of graphene membrane over micropore. C) Nanopore fabrication procedure. For graphene nanopore, a pulsing procedure was used, which was terminated at reaching a predetermined trigger level. For SiN membranes, a constant voltage procedure was used (not shown). D) A transmembrane voltage Vm is applied and the ion current I (dashed) is measured as DNA (green) translocates through a nanopore from the cis to trans side.

We used the wedge transfer technique developed by Schneider et al. to transfer and deposit individual graphene flakes onto micropores. We covered individual graphene flakes in a droplet of Cellulose Acetate Butyrate (CAB, Sigma-Aldrich 419036-250G) in Ethyl Acetate (EtAc, Sigma Aldrich 319902-1L) mixture, with its location manually marked. The graphene flake and CAB transfer polymer were wedged off from its Si/SiO₂ substrate in de-ionized water with a freshly aspirated surface, before transferred onto a hydrophilic micropore treated with RF oxygen plasma for three minutes (Harrick Plasma PDC-32G, 18 W). Under an optical microscope with a modified stage, the graphene flake and CAB was manually positioned over the micropore before residual water completely dried. After ensuring the graphene was placed correctly (FIG. 11), the micropore with graphene under CAB was placed on a hotplate at 75° C. for 30 min to promote secure adhesion. The CAB was dissolved in two separate EtAc baths for 30 s. The remaining graphene flake was deposited onto the micropore by annealing at 400° C. for 30 min. Suspended graphene samples were imaged in a Transmission Electron Microscope (FEI Titan S/TEM) (FIG. 11).

SiN samples were acquired commercially and cleaned with Piranha Etch and treated with RF oxygen plasma.

A custom microfluidic flow cell was immersed in DI water with its channels pre-flushed to remove residual air. Assembled devices were immersed in ethanol (EtOH, PHARMCO-AAPER, 111000200) to remove trapped air inside the micropore pyramid. The pre-wetted device was transferred and mounted in the flow cell under water. Once removed from water, the mounted device was secured and the outside of the cell was dried thoroughly before both channels were flushed with 2 M KCl buffer solution for initial I(V) measurements.

C. Nanopore Fabrication

Once membranes were confirmed to be insulating, nanopores were fabricated in both SiN and graphene membranes using dielectric breakdown. Graphene pores were formed by rapid pulses of increasing duration Δt and height ΔV. Depending on the desired pore size, we simultaneously observed whether R exceeded 10-20 MΩ at 0.2 V. Initial pulses were Δt=1 µs long and ΔV=3 V high. Then ΔV was slowly increased up to 10 V. If no initial pore was formed, ΔV was reduced and Δt was increased. Nanopores formed at 6-10 V at 1 µs–1 ms. Upon initial pore formation, pulses at 3-4 V of similar duration as initial formation were used to adjust the nanopore diameter d (FIG. 11).

SiN nanopores were made by slowly ramping a constant bias V until a desired trigger current level I was reached. The pore was enlarged by resetting V and ramping up again, and the trigger level was reached at decreasing V levels. Initial trigger currents were I=30-80 nA and initial formation occurred at V=4-6 V. Post breakdown enlarging caused triggering to occur below ~1 V.

An initial value of the nanopore diameter d was determined from the open pore conductance G using the bare pore conductance G₀ and access resistance Ra:

$$G = \left(G_0^{-1} + R_a\right)^{-1} \quad (1)$$

$$G_0 = \underbrace{\frac{\pi d^2}{4L_{pore}}(\mu_K + \mu_{Cl})en_{KCl}}_{=\sigma} + \frac{\pi \mu_K \sigma_q d}{L_{pore}}$$

$$R_a = \frac{1}{\sigma d}$$

Note that $\sigma_q$ is surface charge density while $n_{KCl}$ conductivity is $\sigma$. The pore diameter d and depth $L_{pore}$ were determined self consistently using $G(n_{KCl}=2\ M)$ and $\Delta G(n_{KCl}=2\ M)$.

D. Buffers and DNA

2 M KCl buffer solution was made with 2 M KCl, 10 mM Tris HCl, and 1 mM EDTA. Additionally, Lambda DNA (N3011L, New England Biolabs) and KCl buffers with an initial pH~5. When changing $n_{KCl}$ from 2 M to a lower value, we track G vs. t and wait until it saturates at a value consistent with Eq. 1. We do not see a contribution from $\sigma_q$ in these experiments, which we comment on below. Experiments were performed at room temperature.

E. Data Acquisition & Analysis

The cis-channel of the flow cell was flushed with lambda DNA solutions at selected KCl concentrations. The trans-channel flushed with selected KCl concentration only. A trans-membrane voltage Vm was applied to electrophoretically drive the DNA through the nanopore. For SiN at all $n_{KCl}$ values Vm≤100 mV, while Vm≤200 mV for graphene nanopores. The corresponding ion current change was recorded (FIG. 6) with a data acquisition board (National Instruments PCI-6251) and custom acquisition software at 0.1-1.25 MS/s, with a Fourier filter to remove stray interference.

To filter out low-current signal events in the presence of a high 1/f-noise background, common in nanopore systems, we detected events as follows. The signal is leveled by subtracting a 100-point convolution average. The standard deviation is recorded for every 100-point section of the leveled signal, i. e. the background $I_{bg}$, with the median standard deviation $\sigma_m$ of that set recorded as well. Possible events were identified as exceeding $I_{bg}$ by a multiple of $\sigma_m$, without yielding false positives: 3 to 5 $\sigma_m$. The signal was then convolved with a 2-point average, before the procedure repeated. Subsequently, events were fitted with the expected rectangular shape of height $\Delta I$ and duration $\tau$ of translocation waveforms, deduplicated, and reduced based on the $X^2$ values and signal to noise ratio $\Delta I/\sigma_m$.

This manner of event detection is particularly useful for detecting low-signal events against a high 1/f background. The convolution filter preserves the squareness of the event waveform so it is not distorted when large parts of the spectrum are rejected. Furthermore, the ratio of the shortest timebase $\tau s$ (reduced timebase due to convolution) to longest timebase $\tau l$ (100 point baseline subtraction) gives a constant bandwidth ratio that returns constant noise RMS values:

$$\sigma_m^2 \approx C_{LF} I_{DC}^2 \log(\tau_l/\tau_s)$$

when 1/f noise dominates. This facilitates a numerical threshold criterion that does not depend on the part of the spectrum under consideration. For graphene nanopores we find $CLF \approx 10^{-5}$ to $10^{-3}$ with no clear $n_{KCl}$ dependence, while for SiN nanopores we find $CLF \approx 10^{-4}$ to $10^{-3}$ at $n_{KCl}=2.0$ M with a monotonic increase of a factor$\approx 10$ down to $n_{KCl}=10$ mM.

III. OBSERVATIONS

We observe a series of short changes in the ion conductance $\Delta G$ across the nanopore (FIG. 6) every time a DNA molecule translocates through the pore. To ensure these fluctuations are well separated from the baseline current $I_{bg}$ and display a distinctive peak in the ion current histogram, we limit the passage of folded molecules by fabricating relatively small nanopores, d=4 . . . 7 nm. At high $n_{KCl}$, we normally find $\Delta G<0$ because it is dominated by the exclusion of ions from the nanopores.

Conversely at low $n_{KCl}$, $\Delta G>0$, since counterion current from the DNA backbone dominates. Both effects are described by $$\Delta G_{pore} = \left( \underbrace{-\frac{\pi}{4} d_{DNA}^2 \sigma' \mu_R}_{\text{exclusion}} + \underbrace{\mu_K^* q_{L,DNA}^*}_{\text{backbone}} \right) / L_{pore}. \quad (2)$$

Due to the charge q* and cross-section $\pi d^2/4$ of dsDNA being halved during denaturation or unzipping, its conductance is also halved:

$$\Delta G_{pore,ssDNA} = \tfrac{1}{2} \Delta G_{pore}.$$

Over a range of $n_{KCl}$ concentrations, the expected conductance values of dsDNA (black) and ssDNA (blue) are shown in FIG. 6 and are directly compared to our observations.

Figure 12:
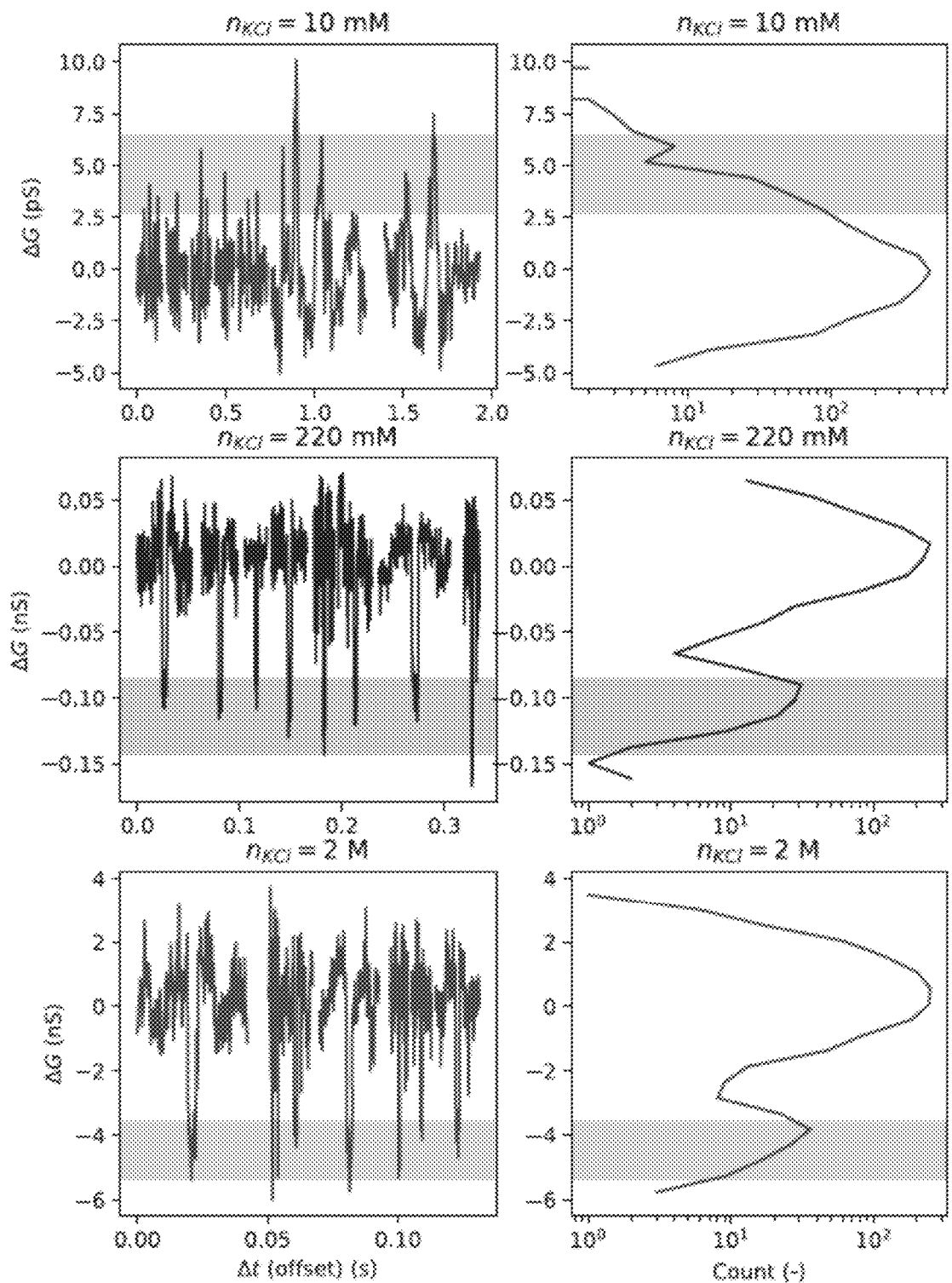
FIG. 12 shows unzipping of high-molecular-weight DNA through graphene nanopores. Left: Subset of ΔG for events at nKCl=0.010, 1, and 2 M. Right: Histogram of all event current traces for corresponding conditions in left panel with secondary peak width (shaded).

We observe two major deviations from Eq. 2 for SiN and graphene nanopores. The first deviation occurs between expected values between $n_{KCl}$ and $\Delta G$. With pore diameters between d=5-7 nm, SiN nanopores observed at lower $n_{KCl}$ had $\Delta G$ values significantly smaller than Eq. 2 predicts. For graphene nanopores with diameters between d=4-7 nm, we observe an overall trend of $\Delta G>0$ at high $n_{KCl}$ and $\Delta G<0$ at low $n_{KCl}$. However, we also observe at $n_{KCl}\sim 220$ mM, $\Delta G<0$ in contrast to the prediction of $\Delta G>0$ from Eq. 2 (FIG. 12). Specifically, FIG. 12 shows unzipping of high-molecular-weight DNA through graphene nanopores. Left: Subset of $\Delta G$ for events at $n_{KCl}=0.010$, 1, and 2 M. Right: Histogram of all event current traces for corresponding conditions in left panel with secondary peak width (shaded).

Figure 13:
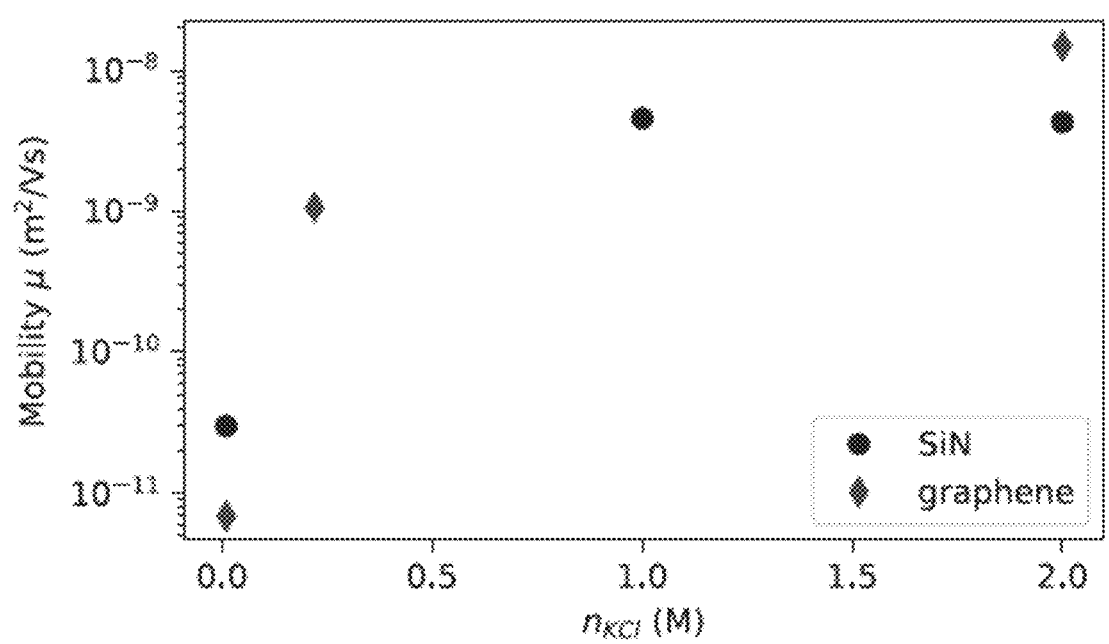
FIG. 13 shows the mobility of DNA driven through graphene (red diamonds) and SiN nanopores (blue circles) as a function of nKCl.

The second deviation occurs with reduced mobility μ. While we designed our graphene nanopores to deliberately be treated without a passivation layer to inhibit ssDNA binding due to pi-stacking interactions, at $n_{KCl}=10$ mM we see translocation events with $\Delta G>0$ and much reduced μ (FIGS. 12 and 13). Simultaneously, we see a slow decrease in background current $I_{bg}$ and therefore an increase of background resistance R in a linear manner at a rate of $dR/dt \approx 10\%/\text{min}$. We do not see an exponential dependence within ~5 min. This increase is only visible at forward bias, Vm>0, not reverse bias. When applying reverse bias pulses with duration and height typical for pore enlargement, the conductance does not recover. In contrast at higher $n_{KCl}$, the background resistance is stable and there is an upper limit to the R drift, i. e. $|dR/dt| \leq 0.5\%$. The increase of R at low $n_{KCl}$ ultimately limits the duration of the experiment and lifetime of graphene devices, and we do not observe this with SiN nanopores.

FIG. 13 shows the mobility of DNA driven through graphene (red diamonds) and SiN nanopores (blue circles) as a function of nKCl.

For both SiN and graphene nanopores, we studied the mobility μ of DNA driven through the nanopore. Mobility was determined as μ=v/E, where v is the translocation speed and E the effective field in the nanopore (FIG. 13). We used $E=V_{eff}/L_{pore}$, where $V_{eff}$ is the voltage drop across $G_0+\Delta G_{pore}$ in a series $1/(G_0+\Delta G_{pore})+Ra$ network that divides down the applied voltage Vm. Typical field strengths were 2 MV m$^{-1}$ for SiN and 20 MV m$^{-1}$ for graphene. At high ionic strengths, we find typical μ for DNA in both graphene and SiN nanopores. However, at 10 mM, μ is reduced by a factor ~100, for both SiN and graphene nanopores.

IV. DISCUSSION

A. SiN Nanopores

The role of $R_a$

The values for $\Delta G$ at low $n_{KCl}$ are much lower than Eq. 2 describes (FIG. 6). We argue that in a low $n_{KCl}$ regime, the effect of access resistance Ra must be taken into account. When the pore is open, Ra and $1/G_0$ constitute a voltage divider, whereas when DNA is inside the pore, Ra and $1/(G_0+\Delta G_{pore})$ constitutes one. If $d \ll L_{pore}$ at high $n_{KCl}$, most of the voltage drops across the pore and $\Delta G$ follows Eq. 2. However, at low $n_{KCl}$ the geometric dependence of $\Delta G_{pore}$ changes and the condition $d \ll L_{pore}$ no longer guarantees $Ra \ll (G_0+\Delta G_{pore})^{-1}$. Consequently, the quantity actually measured is:

$$\Delta G = [R_a + (G_0+\Delta G_{pore})^{-1}]^{-1} - (R_a+G_0^{-1})^{-1} \quad (3)$$

(FIG. 6). We extract $\Delta G_{pore}$ using the inverse of Eq. 3, causing the ssDNA and dsDNA curves at low $n_{KCl}$ to separate (FIG. 6) and observe a distinct grouping of $\Delta G_{pore}$ on the ssDNA curves.

The Role of $\sigma_q$

We do not see a contribution of surface charge σq to the open pore conductance G of our nanopores. While this is expected for graphene, for SiN in our experiments σq~0 since we operated close to the charge neutrality point pH~4.1. Alternatively, we could have non-zero σq if $n_{KCl}$ is different than expected. We use the settling of G to an expected value according to $n_{KCl}$ as an indicator that we reached the right concentration. It can be argued that due to residual $n_{KCl}$, a higher $n_{KCl}$ is actually reached. However, that also increases G. Another argument could incorporate σq by assuming $n_{KCl}$ is much lower than introduced. However, in our experience, exchanging high $n_{KCl}$ for lower $n_{KCl}$ only appears to lead to slightly higher $n_{KCl}$ than desired, if fresh solvent is not used enough and/or we do not wait long enough. Pore shrinkage combined with a higher effective $n_{KCl}$ together could allow for a finite σq that would explain our open pore conductance values. However, we confirm that SiN pores usually do not shrink by going back to the starting $n_{KCl}$ and finding the same open pore conductance. [We note that if $n_{KCl}$ were higher, it would also significantly reduce the unzipping capability]. A final alternative interpretation is that we have a source of contamination on the SiN membranes, despite our exhaustive cleaning the membranes with organic solvents, oxygen plasma, and Piranha, We calibrate the pore geometry as described and find $L_{pore}$=20-40 nm larger than the bare membrane. If this is due to an accumulation of material that does not contribute to σq that would be consistent with our observations.

Halving of $\Delta G_{pore}$

As $\Delta G_{pore}$ is on the ssDNA curve (FIG. 6), we suspect that we are translocating single strands despite starting with high-MW double strands. Under physiological conditions, the two strands of dsDNA bind together because the hydrogen bonds and stacking energies are stronger than the effective electrostatic repulsion of the two negatively charged backbones. This repulsion is overcome because the cations screen the backbone with a Debye length:

$$\lambda_D = \sqrt{\epsilon k_B T/2e^2 n_{KCl}},$$

where E is the permittivity, kB is Boltzmann's constant, T is the absolute temperature, and e is the electron charge. At room temperature $\lambda D(n_{KCl}=1 M)=0.3$ nm while $\lambda D(n_{KCl}=10 mM)=3.0$ nm, which exceeds the distance between the backbones. This effect favors the separation of the dual strands and lowers the melting temperature Tm. However, Tm for high-MW dsDNA at $n_{KCl}$=10 mM is usually around 70° C. and depends on sequence.

We hypothesize that we are unzipping the dsDNA due to the large E field at the pore. While the unzipping or force-induced melting of dsDNA is a well-studied subject, the nanopores used previously are usually smaller than the dsDNA size (<2 nm) and very short DNA (~50 b) strands are typically employed. When ~5 kb strands are used, secondary structures cause large blockage signatures and a slowdown of the translocation process. Here, we appear to drive high-molecular-weight ssDNA through a nanopore without secondary structures. The energetics of the unzipping process are usually analyzed using a Kramers-type 1D escape problem. An applied force f acts over a range Δx in overcoming the barrier, such that:

$$\tau = \tau_0 \exp((E_b - f\Delta x)/k_B T) \quad (4)$$

Using a hydrogen bond range of Δx≈0.6 nm, a field strength of E≈8.3 MV m$^{-1}$, an effective charge of:

$$q = \frac{1}{4}e$$

per base, we find f Δx=0.05 $k_B$T. Once unzipping has started under physiological conditions, it takes ~0.1 $k_B$T to break each additional pair, well within range of the available energy, Under this scenario, the capture rate could be limited by the initial energy barrier to get the unzipping going, afterwards the process is downhill.

Unzipping Selection Mechanism

We are using nanopores that are in principle large enough to accommodate both strands simultaneously. In fact, we use the dsDNA signal to calibrate d and $L_{pore}$ in situ. Without a selection mechanism, dsDNA is as likely to translocate as unzipped ssDNA. How is it then possible that we appear to translocate unzipped single stranded molecules? First, since we see few, if any, folded and/or double strand signals, we assume the dominant capture mode is end-capture. In addition to small d, folded capture is also limited by the much larger persistence length Lp at low ionic strength. Second, since we are close to Tm, denaturing bubbles are expected to cause a rapid time dependent fraying of the ends of the molecule.

We put forward two considerations. First, the individual frayed strands at the molecule's end are expected to fluctuate more than the common mode double strand fluctuations due to the much-reduced Lp of ss over dsDNA, even at low ionic strength. If this constitutes an increase in attempt frequency for capture, this would favor unzipping. Second, if the pore is charged and that charge is poorly screened, it could renormalize d thus favoring passage of single over double strands. However, we do not see a role of aq for SiN pores and do not believe that surface charge of the pore plays a role in unzipping. We posit that the preferential trapping of the frayed single strands is the selection mechanism responsible for unzipping over double-strand translocation. A compounding mechanism could be envisioned that works similarly to geometric selection, i.e. denaturation bubbles are larger than fully hybridized dsDNA. Due to that size being close to d, dsDNA could be prevented from entering the pore. While the bubble size is most likely limited to the hydrogen bond length of 0.6 nm for few-base bubbles, it may be larger at the frayed end of dsDNA. Experiments at larger d could elucidate the role of this effect.

Grouping of Translocation Events

It is possibly expected that once a single strand has translocated, its complement would be captured quickly afterwards, which could cause a grouping in inter-translocation times. The two strands would translocate quickly after one another, followed by translocation of another molecule at a longer time. We do not see such a grouping which may be due to the large scatter in inter-event times.

B. Graphene Nanopores

ΔG for Graphene Nanopores

ΔG does not appear to follow Eq. 2, especially at $n_{KCl}$=220 mM where the sign of ΔG is opposite from that expected (FIG. 12). We argue that the particular geometry of our graphene nanopores have an effect on ΔG. Specifically, we have a significantly lower aspect ratio $\alpha = L_{pore}/d$ in our graphene nanopores than in SiN nanopores. This causes Ra to dominate the nanopore resistance resulting in G∝d, instead of G∝d².

Continuum modeling shows that the current density $j_i$ is carried mostly at the perimeter of the nanopore. Moreover, non-uniform j can also be expected due to the local dipole moments at the graphene nanopore edge. The crossover $n_{KCl}$* deduced from Eq. 2 assumes uniform $j_i$ inside the nanopore. Since $j_i$ is not uniform, but carried at the nanopore perimeter, we must compare the counter-ion current density $j_c$ with $j_i$ and integrate over the DNA cross-section. For small nanopores, such as the ones studied in this paper, a significant part of the DNA's cross section is blocking the higher $j_i$ at the pore edge. This would push:

$$n^*_{KCl}$$

lower and could explain why we observe ΔG<0. For larger nanopores and α, if the point of translocation is approximately in the center of the nanopore, the blocked $j_i$ is lower than the uniform $j_i$ and push:

$$n^*_{KCl}$$

higher. However, a thorough experimental and theoretical evaluation of this effect has not been reported before and is beyond the scope of this report.

Selection Mechanism for Graphene

Specifically for unzipping at graphene pores, the pi bonding could cause one of the strands to be tied to the graphene, freeing up the other strand for translocation. However, we see similar μ at low $n_{KCl}$ with graphene, which does not carry a major surface charge save for some dipoles at the nanopore edge, e. g. carboxyl groups.

$I_{bg}$ Reduction at Low $n_{KCl}$ in Graphene

As the reduction does not appear in SiN pores at low $n_{KCl}$ and only at forward bias with graphene pores, the decrease is consistent with a very slow binding of DNA material close to the pore. As the binding does not appear reversible by voltage pulsing, pi-bonding of free bases in denaturation bubbles to the hexagonal graphene lattice is a logical candidate. Close to the nanopore, we expect E to be stronger in graphene pores owing to the much smaller $L_{pore}$, even when factoring in the larger role of Ra. Furthermore, if unzipping occurs at SiN due to E, it is reasonable to expect it does so for graphene nanopores as well.

Both SiN and Graphene Nanopores

Single Nanopores

The breakdown method of making nanopores requires nucleation of a defect, followed by a slow opening of the pore through the same defect. It is possible that we have more than a single defect and rather than opening a single defect, we are opening two or more defects. However, if we allow for a parallel current path and use that to solve for the pore geometry, we do not get self-consistent results. Therefore, we conclude we only measure single nanopores.

Mobility Reduction

This may be expected due to the unzipping introducing a rate limit. We can quantify the rate with Equation 4 but the attempt frequency is difficult to determine independently for the complicated nanoelectro-mechanical landscape in the vicinity of the pore and is subject of further studies. The mobility reduction can also be due to DNA adhering to the substrate and could explain the lower μ for graphene than SiN. Indeed, the ~10 fold reduction for graphene at 220 mM could be due to DNA adhesion, as well. However, since the largest share of reduction in μ is similar for both types of pores, we hypothesize the unzipping itself is primarily responsible for lowering μ, as has been observed in space-constricted unzipping in smaller nanopores.

V. CONCLUSIONS

We present evidence of unzipping high-MW DNA in situ due to the strong field at a nanopore entrance and translocating single strands without secondary structure, resulting in a ~100-fold reduction in μ. Despite the pores being large enough to accommodate both strands, we preferentially capture single strands at the frayed ends of the DNA. We hypothesize that single end capture mechanism is due to an increased attempt frequency for capture for single over double strands owing to the much shorter persistence length.

For follow-up studies, we plan to explore the phase diagram of the unzipping process. First, raising the cell temperature to Tm should yield unambiguous melted DNA and therefore a clear ΔG at the same $n_{KCl}$ that we can compare to. Second, the trade-off between E and proximity to Tm represents a 2D phase diagram in which more points can be chosen to determine the phase boundary. Third, adjusting the pH value to alter the surface charge of the SiN surface and allow an independent inspection of the role of σq. Fourth, further exploring the unzipping speed scale with energy barrier once the bias is factored in, as a function of proximity to Tm. Fifth, distinguishing event signals between blunt end and single-stranded overhang translocations. Finally, determining the role of larger nanopore diameters in unzipping and single-stranded translocation.

REFERENCES

Akeson, M., Branton, D., Kasianowicz, J. J., Brandin, E., and Deamer, D. W. (1999). Microsecond time-scale discrimination among polycytidylic acid, polyadenylic acid, and polyuridylic acid as homopolymers or as segments within single RNA molecules. Biophysical journal, 77(6): 3227-33.

Amorim, R. G., Rocha, A. R., and Scheicher, R. H. (2016). Boosting DNA Recognition Sensitivity of Graphene Nanogaps through Nitrogen Edge Functionalization. The Journal of Physical Chemistry C.

Bunch, J. S., Verbridge, S. S., Alden, J. S., van der Zande, A. M., Parpia, J. M., Craighead, H. G., and McEuen, P. L. (2008). Impermeable Atomic Membranes from Graphene Sheets. Nano Letters, 8(8):2458-2462.

Butler, T. Z., Gundlach, J. H., and Troll, M. A. (2006). Determination of RNA Orientation during Translocation through a Biological Nanopore. Biophysical Journal, 90(1):190-199.

Chang, S., He, J., Kibel, A., Lee, M., Sankey, O., Zhang, P., and Lindsay, S. (2009). Tunnelling readout of hydrogen-bonding-based recognition. Nature Nanotechnology, 4:297.

Deamer, D. W. and Branton, D. (2002). Characterization of nucleic acids by nanopore analysis. Acc. Chem. Res, 35(10):817-825.

Dekker, C. (2007). Solid-state nanopores. Nat. Nanotechnol, 2:209-215.

Hall, J. E. (1975). Access resistance of a small circular pore. Journal of General Physiology, 66(4):531.

Kasianowicz, J., Brandin, E., Branton, D., and Deamer, D. W. (1996). Characterization of individual polynucleotide molecules using a membrane channel. Proc. Nati. Acad. Sci., 93(24):13770-13773.

Koenig, S. P., Boddeti, N. G., Dunn, M. L., and Bunch, J. S. (2011). Ultrastrong adhesion of graphene membranes. Nat Nano, 6:543-546.

Kowalczyk, S. W., Tuijtel, M. W., Donkers, S. P., and Dekker, C. (2010). Unraveling Single-Stranded DNA in a Solid-State Nanopore. Nano Letters, 10(4):1414-1420.

Lee, C., Wei, X., Kysar, J. W., and Hone, J. (2008). Measurement of the Elastic Properties and Intrinsic Strength of Monolayer Graphene. Science, 321(5887):385-388.

Li, J., Stein, D., McMullan, C., Branton, D., Aziz, M. J., and Golovchenko, J. A. (2001). Ion-beam sculpting at nanometre length scales. Nature, 412(6843):166-169.

Meller, A., Nivon, L., Brandin, E., Golovchenko, J., and Branton, D. (2000). Rapid nanopore discrimination between single polynucleotide molecules. Proceedings of the National Academy of Sciences, 97(3):1079-1084.

Meller, A., Nivon, L., and Branton, D. (2001). Voltage-Driven DNA Translocations through a Nanopore. Physical Review Letters, 86(15):3435.

Ohshiro, T., Matsubara, K., Tsutsui, M., Furuhashi, M., Taniguchi, M., and Kawai, T. (2012).

Single-molecule electrical random resequencing of DNA and RNA. Scientific reports, 2:501.

Ohshiro, T., Tsutsui, M., Yokota, K., Furuhashi, M., Taniguchi, M., and Kawai, T. (2014). Detection of post-translational modifications in single peptides using electron tunnelling currents. Nature Nanotechnology, 9(10):835-840.

Patel, H. N., Carroll, I., Jr, R. L., Sankararaman, S., Etienne, C., Kodigala, S. R., Paul, M. R., and Postma, H. W. C. (2017). DNA-graphene interactions during translocation through nanogaps. PLOS ONE, 12(2):e0171505.

Poot, M. and van der Zant, H. S. J. (2008). Nanomechanical properties of few-layer graphene membranes. Applied Physics Letters, 92(6):063111-3.

Postma, H. W. C. (2008). Rapid Sequencing of Individual DNA Molecules in Graphene Nanogaps. arxiv.org/abs/0810.3035.

Postma, H. W. C. (2010). Rapid Sequencing of Individual DNA Molecules in Graphene Nanogaps. Nano Letters, 10(2):420-425.

Prasongkit, J., Feliciano, G. T., Rocha, A. R., He, Y., Osotchan, T., Ahuja, R., and Scheicher, R. H. (2015). Theoretical assessment of feasibility to sequence DNA through interlayer electronic tunneling transport at aligned nanopores in bilayer graphene. Scientific Reports, 5.

Prasongkit, J., Grigoriev, A., Pathak, B., Ahuja, R., and Scheicher, R. H. (2011). Transverse Conductance of DNA Nucleotides in a Graphene Nanogap from First Principles. Nano Letters, 11(5):1941-1945.

Scarpa, F., Adhikari, S., and Phani, A. S. (2009). Effective elastic mechanical properties of single layer graphene sheets. Nanotechnology, 20(6):065709.

Smeets, R. M. M., Keyser, U. F., Krapf, D., Wu, M.-Y., Dekker, N. H., and Dekker, C. (2006). Salt Dependence of Ion Transport and DNA Translocation through Solid-State Nanopores. Nano Letters, 6(1):89-95.

Storm, A. J., Chen, J. H., Zandbergen, H. W., and Dekker, C. (2005). Translocation of doublestrand DNA through a silicon oxide nanopore. Physical Review E, 71(5): 051903.

Tsutsui, M., Taniguchi, M., Yokota, K., and Kawai, T. (2010). Identifying single nucleotides by tunnelling current. Nat Nano, 5(4):286-290.

SEQUENCE LISTING

There is no new matter entered as part of this Sequence Listing. The ASCII Text File named "SequenceListingTextASCII" created on May 1, 2022 with a size of 303 bytes is incorporated herein by reference. Support for this section is found on page 27 herein.

Thus, specific embodiments, methods of devices, methods, and processes for single-molecule sequencing have been disclosed. It should be apparent, however, to those skilled in the art that many more modifications besides those already described are possible without departing from the inventive concepts herein. The inventive subject matter, therefore, is not to be restricted except in the spirit of the disclosure herein. Moreover, in interpreting the specification and claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

I claim:

1. A process for conductive material nanogap formation, comprising:
   providing a base material, wherein the base material comprises a micropore that extends through a first layered material, and wherein the micropore comprises a top opening, a bottom opening, and a volume boundary,
   applying a conductive material sheet to the first layered material, wherein the conductive material sheet covers the top opening of the micropore,
   applying two conducting electrodes to the conductive material sheet, so that each one of the conducting electrodes is positioned on either side of the micropore,
   applying an etch mask that covers at least a part of the conductive material sheet, the top opening of the micropore, or a combination thereof,
   applying a passivation layer over at least the etch mask,
   fabricating a hole in the passivation layer directly above the top opening of the micropore, and
   applying at least one voltage pulse through the at least one conducting electrode to create a nanogap in the conductive material sheet, wherein the nanogap is over and open to the top opening of the micropore.

2. The process of claim 1, further comprising:
   utilizing the two conducting electrodes to determine the width of the nanogap in the conductive material sheet.

3. Process of claim 1, wherein the conductive material sheet comprises graphene.

4. The process of claim 1, wherein the etch mask also covers at least one of the conducting electrodes.

5. The process of claim 1, wherein the base material comprises at least two layers.

6. The process of claim 5, wherein the at least two layers may comprise a substrate, a thin membrane that is applied to or coupled with the substrate to form a first layered material, at least one insulating layer, at least one additional layer of material, or a combination thereof.

7. Process of claim 1, wherein the at least one conducting electrode is positioned at least a first distance away from the volume boundary of the micropore.

8. The process of claim 1, wherein the conductive material sheet is heated above an ambient temperature before fabricating a hole in the passivation layer directly above the top opening of the micropore.

9. A nanogap in a conductive material sheet formed by the process of claim 1, wherein the nanogap comprises a top side and a bottom side and comprises a width.

10. The nanogap of claim 9, comprising a first distance on the conductive material sheet between an edge of the nanogap and an edge of an insulating material.

11. The nanogap of claim 10, wherein the top side and the bottom side of the nanogap, along with the first distance is accessible and able to interact with a liquid.

12. A macromolecule translocation device, comprising the nanogap of claim 9, wherein the device is a nonlinear conductor.

13. The macromolecule translocation device of claim 12, wherein the device utilizes a mixing technique, the mixing technique comprises:
   providing a first high frequency source having a frequency f to the device,
   providing a second high frequency source having a frequency f+$\Delta$f to the device,
   mixing the first high frequency source frequency with the second high frequency source frequency to yield a first signal at 2f+$\Delta$f and a second signal at x$\Delta$f, wherein x is an integer.

14. A process for conductive material nanogap formation, comprising:
   providing a base material,
   applying a conductive material sheet to the base material,
   applying two conducting electrodes to the conductive material sheet,
   applying an etch mask that covers the at least one conducting electrode and at least a part of the conductive material sheet to form a first layered material,
   applying a first insulating layer to the first layered material to form a second layered material,
   fabricating a micropore in the second layered material, and
   simultaneously fabricating a nanogap in the conductive material sheet, wherein the nanogap is smaller in diameter than the micropore.

15. The process of claim 14, wherein the conductive material sheet comprises graphene.

16. The process of claim 14, wherein the etch mask also covers at least one of the conducting electrodes.

17. The process of claim 14, wherein the base material comprises at least two layers.

18. The process of claim 17, wherein the at least two layers may comprise a substrate, a thin membrane that is applied to or coupled with the substrate to form a first layered material, at least one insulating layer, at least one additional layer of material, or a combination thereof.

19. A nanogap in a conductive material sheet formed by the process of claim 14, wherein the nanogap has a width.

20. The nanogap of claim 19, comprising a first distance on the conductive material sheet between an edge of the nanogap and an edge of an insulating material.

21. The nanogap of claim 20, wherein the top side and the bottom side of the nanogap, along with the first distance is accessible and able to interact with a liquid.

22. A macromolecule translocation device, comprising the nanogap of claim 19, wherein the device is a nonlinear conductor.

23. The macromolecule translocation device of claim 22, wherein the device utilizes a mixing technique, the mixing technique comprises:
   providing a first high frequency source having a frequency f to the device,
   providing a second high frequency source having a frequency f+$\Delta$f to the device,
   mixing the first high frequency source frequency with the second high frequency source frequency to yield a first signal at 2f+$\Delta$f and a second signal at x$\Delta$f, wherein x is an integer.

* * * * *

SEQUENCE LISTING

```
<160> NUMBER OF SEQ ID NOS: 1

<210> SEQ ID NO 1
<211> LENGTH: 29
<212> TYPE: DNA
<213> ORGANISM: Unknown
<220> FEATURE:
<221> NAME/KEY: Unsure
<222> LOCATION: (1)...(29)
<223> OTHER INFORMATION: Artificial simulation of a sequence for
      modeling
<300> PUBLICATION INFORMATION:

<400> SEQUENCE: 1
cggcgagtag cataagcgag tcatgttgt                                    29
```